(12) United States Patent
Hussey

(10) Patent No.: US 11,636,006 B2
(45) Date of Patent: Apr. 25, 2023

(54) SYSTEM AND METHOD FOR MODULAR CONSTRUCTION OF EXECUTABLE PROGRAMS HAVING SELF-CONTAINED PROGRAM ELEMENTS

(71) Applicant: Chewy, Inc., Dania Beach, FL (US)

(72) Inventor: Benjamin Hussey, Chicago, IL (US)

(73) Assignee: Chewy, Inc., Dania Beach, FL (US)

( * ) Notice: Subject to any disclaimer, the term of this patent is extended or adjusted under 35 U.S.C. 154(b) by 0 days.

(21) Appl. No.: 17/583,942

(22) Filed: Jan. 25, 2022

(65) Prior Publication Data
US 2022/0283893 A1 Sep. 8, 2022

Related U.S. Application Data

(60) Provisional application No. 63/156,205, filed on Mar. 3, 2021.

(51) Int. Cl.
*G06F 11/00* (2006.01)
*G06F 11/07* (2006.01)
(Continued)

(52) U.S. Cl.
CPC ...... *G06F 11/0793* (2013.01); *G06F 11/1402* (2013.01); *G06V 30/414* (2022.01); *G16H 20/10* (2018.01)

(58) Field of Classification Search
CPC .................. G06F 11/0793; G06F 11/1402
See application file for complete search history.

(56) References Cited

U.S. PATENT DOCUMENTS 7,114,154 B1 9/2006 Crohn
7,117,480 B2 10/2006 Andersh et al.
(Continued)

FOREIGN PATENT DOCUMENTS

WO 97/44729 11/1997

OTHER PUBLICATIONS

International Search Report and Written Opinion for International Application No. PCT/US2022/018619 dated Jun. 29, 2022.

*Primary Examiner* — Joshua P Lottich
(74) *Attorney, Agent, or Firm* — Morgan, Lewis & Bockius LLP

(57) ABSTRACT

A method for performing a fault tolerant automated sequence of computer implemented tasks including, presenting for selection by a user a plurality of pre-programmed elements, each pre-programmed element being independently executable relative each other pre-programmed element, receiving from the user a selection of one or more of the pre-programmed elements and a sequence for performing each pre-programmed element to form an exemplary routine, creating an instance of the exemplary routine, the instance of the exemplary routine including an instance of each of the selected pre-programmed elements arranged for performance in accordance with the sequence and configured to perform tasks defined by the pre-programmed elements and the sequence, initiating implementation of the instance of the exemplary routine by initiating performance of the instances of the pre-programmed elements in accordance with the sequence, and executing each instance of the pre-programmed elements according to the sequence.

26 Claims, 22 Drawing Sheets

(51) Int. Cl.
*G06V 30/414* (2022.01)
*G16H 20/10* (2018.01)
*G06F 11/14* (2006.01)

(56) References Cited

U.S. PATENT DOCUMENTS

| | | | |
|---|---|---|---|
| 7,363,594 | B1 | 4/2008 | Wright et al. |
| 7,590,835 | B1 * | 9/2009 | Nallagatla ........... G06F 9/44505 |
| | | | 717/169 |
| 7,630,965 | B1 | 12/2009 | Erickson et al. |
| 8,448,136 | B2 | 5/2013 | Mills et al. |
| 8,924,269 | B1 | 12/2014 | Seubert et al. |
| 9,595,014 | B1 | 3/2017 | Vohra et al. |
| 2003/0135842 | A1 * | 7/2003 | Frey .......................... G06F 8/71 |
| | | | 717/121 |
| 2004/0249695 | A1 | 12/2004 | Clark et al. |
| 2007/0236509 | A1 * | 10/2007 | Eldridge ............... G06F 3/0486 |
| | | | 345/619 |
| 2008/0141076 | A1 * | 6/2008 | Hu ...................... G06F 11/0733 |
| | | | 714/45 |
| 2009/0327942 | A1 * | 12/2009 | Eldridge .............. G05B 19/056 |
| | | | 715/771 |
| 2011/0060895 | A1 * | 3/2011 | Solomon .................... G06F 8/36 |
| | | | 713/1 |
| 2012/0041570 | A1 | 2/2012 | Jones et al. |
| 2013/0036350 | A1 | 2/2013 | Arbo |
| 2014/0222181 | A1 * | 8/2014 | Hemenway ......... G06F 3/04817 |
| | | | 700/97 |
| 2020/0097357 | A1 * | 3/2020 | Shwartz ................... G06F 8/70 |

\* cited by examiner

| ID | Molecule | requireContact | Required Atom | requireIncident | requireOrg | Sequence Number |
|---|---|---|---|---|---|---|
| 4 | cancelpetscriptionsrelease | No | cancelpetscriptionsrelease | Yes | No | 1 |
| 5 | cancelpetscriptionsrelease | No | cancelpetscriptionsreleasesendemail | Yes | No | 2 |
| 16 | cancelpetscriptionsrelease | No | orgIsDigital | No | No | 1 |
| 17 | cancelpetscriptionsrelease | No | orgIsDigital | No | No | 2 |

FIG. 2B

```
case 'cancelpetscriptionsrelease':
    require_once(D0CR00T . '/custom/utilities/petscriptions_model.php');
    return $this->processCancelRxOrderInPetscriptions($atom);
    break;
```

| | | |
|---|---|---|
| ID | 200306 | |
| Atom Type | cancelpetscriptionsrelease | |
| Atom State | Complete | |
| Retry Count * | 0 | |
| Molecule Instance * | 155792 | |

| Contact | [No Value] |
|---|---|
| Incident | 200610-003677 |
| Organization | [No Value] |

Associated Data

Audit Log

| | |
|---|---|
| Created By | John Doe |
| Date Created | 06/20/2020 04:02 PM |
| Updated By | Cron Runner |
| Date Last Updated | 06/26/2020 04:03 PM |

| When | Who | What | Source |
|---|---|---|---|
| 06/20/2020 04:03 PM | Cron Runner | Edit | Public API: Connect PHP |
| 06/20/2020 04:02 PM | John Doe | Created | Public API: Custom Process |

Logged in as: John Doe | Editing 3 objects | 06/26/2020 05:44 PM EDT | 100%

```
┌─────────────────────────────────────────────────────────────────┐
│ presenting for selection by a user a plurality of pre-programmed│
│ elements, each pre-programmed element being independently       │─ 1402
│ executable relative each other pre-programmed element such that │
│ an output of any of the pre-programmed elements is not a direct │
│ input to any other of the pre-programmed elements               │
└─────────────────────────────────────────────────────────────────┘
                                 ↓
┌─────────────────────────────────────────────────────────────────┐
│ receiving from the user a selection of one or more of the       │
│ preprogrammed elements and a sequence for performing each       │─ 1404
│ preprogrammed elements in the selection to form an exemplary    │
│ routine                                                         │
└─────────────────────────────────────────────────────────────────┘
                                 ↓
┌─────────────────────────────────────────────────────────────────┐
│ creating an instance of the exemplary routine in response to a  │
│ request to implement the exemplary routine, the instance of the │
│ exemplary routine including an instance of each of the selected │─ 1406
│ pre-programmed elements arranged for performance in accordance  │
│ with the sequence and being configured to perform tasks defined │
│ by the preprogrammed elements and the sequence                  │
└─────────────────────────────────────────────────────────────────┘
                                 ↓
┌─────────────────────────────────────────────────────────────────┐
│ initiating implementation of the instance of the exemplary      │
│ routine by initiating performance of the instances of the pre-  │─ 1408
│ programmed elements in accordance with the sequence             │
└─────────────────────────────────────────────────────────────────┘
                                 ↓
┌─────────────────────────────────────────────────────────────────┐
│ detecting an error that prevents the completion of at least one │─ 1410
│ instance of the pre-programmed elements                         │
└─────────────────────────────────────────────────────────────────┘

┌─────────────────────────────────────────────────────────────────┐
│ terminating the implementation of the instance of the exemplary │─ 1412
│ routine upon detection of the error without user intervention   │
└─────────────────────────────────────────────────────────────────┘
```

SYSTEM AND METHOD FOR MODULAR CONSTRUCTION OF EXECUTABLE PROGRAMS HAVING SELF-CONTAINED PROGRAM ELEMENTS

CROSS-REFERENCE TO RELATED APPLICATIONS

This application claims the benefit of U.S. Provisional Patent Application No. 63/156,205 filed Mar. 3, 2021 entitled "System and Method for Modular Construction of Executable Programs Having Self-Contained Program elements", which is incorporated by reference herein in its entirety.

BACKGROUND OF THE INVENTION

The present invention generally relates to a modular tool for process synchronization programs and, more particularly, to a module tool for construction of computer implemented process synchronization programs, such as programs used to automate customer service tasks.

BRIEF SUMMARY OF THE INVENTION

In one embodiment there is a method for performing a fault tolerant automated sequence of computer implemented tasks comprising presenting for selection by a user a plurality of pre-programmed elements, each pre-programmed element being independently executable relative each other pre-programmed element such that an output of any of the pre-programmed elements is not a direct input to any other of the pre-programmed elements. The method further includes receiving from the user a selection of one or more of the pre-programmed elements and a sequence for performing each pre-programmed elements in the selection to form an exemplary routine. The method further includes creating an instance of the exemplary routine in response to a request to implement the exemplary routine, the instance of the exemplary routine including an instance of each of the selected pre-programmed elements arranged for performance in accordance with the sequence and being configured to perform tasks defined by the pre-programmed elements and the sequence. The method further includes initiating implementation of the instance of the exemplary routine by initiating performance of the instances of the pre-programmed elements in accordance with the sequence and executing each instance of the pre-programmed elements according to the sequence.

In some embodiments, each independently executable pre-programmed element does not require data generated from another pre-programmed element to complete. In some embodiments, each independently executable pre-programmed element completes using data from data field that is at least one of: i) populated in the data field before the creating of the instance of the exemplary routine and ii) updated after the initiating of the implementation of the instance. In some embodiments, the method further includes transmitting a notification that at least one instance of a pre-programmed element did not execute to completion wherein the notification includes at least one of: i) all instance of exemplary routines that are in a failed state at a time the notification is transmitted; ii) the instances of a pre-programmed elements associated with each instance of exemplary routines that are in the failed state; iii) the instance of the exemplary routine; iii) a number of retries associated with each instance of the exemplary routine in the failed state; iv) a database object associated with each instance of the exemplary routine in the failed state.

In some embodiments, the method further includes updating one or more of the pre-programmed elements of the exemplary routine after the initiating implementation step and creating a subsequent instance of the exemplary routine in response to a subsequent request to implement the exemplary routine after the updating step, the subsequent instance of the exemplary routine including an instance of the one or more updated pre-programmed elements of the exemplary routine. In some embodiments, the method further includes simultaneously implementing a plurality of instances of the same exemplary routine. In some embodiments, the method further includes simultaneously implementing at least one instance of the exemplary routine and at least one instance of the subsequent exemplary routine.

In some embodiments, at least some of the instances of the exemplary routine are initiated at a different time than other instances of the same exemplary routine that are being simultaneously implemented. In some embodiments, updating the one or more of the pre-programmed elements includes receiving and storing revised code for performing a task. In some embodiments, the method further includes detecting an error that prevents completion of at least one instance of the pre-programmed elements and terminating the implementation of the instance of the exemplary routine upon detection of the error without user intervention. In some embodiments, the method further includes after the detecting step and before the terminating step, attempting to re-implement at least one instance of the pre-programmed elements associated with the detected error.

In some embodiments, the method further includes detecting a trigger event that triggers, without user intervention, a re-initiation of the performance of the instance of at least one of the pre-programmed elements and wherein an error state that prevents the completion of the at least one instance arises after a subsequent trigger event is detected following a pre-selected number of re-initiations of the performance of the at least one instance of the pre-programmed element. In some embodiments, the method further includes defining a retry threshold value for each of the pre-programmed elements and after the detecting step and before the terminating step, attempting to re-implement the at least one instance of the pre-programmed elements associated with the detected error in accordance with the retry threshold value.

In some embodiments, the method further includes during implementation of the instance of the exemplary routine, detecting the absence of prescription authorization data needed to complete the implementation of the instance of the exemplary routine. The method may further include based on the absence of the prescription authorization, automatically transmitting an authorization form to an authorizing entity, receiving an authorization facsimile of a completed form in response to the automatic transmitting and automatically populating a prescription authorization field based upon the received facsimile. In some embodiments, the method further includes receiving a datafile containing optical character recognition data associated with the authorization facsimile. In some embodiments, the method further includes automatically storing the datafile containing optical character recognition data in a secure database based upon the automatically populating the prescription authorization field.

In some embodiments, regular expression matching logic is applied to the datafile containing optical character recognition data to identify data associated with at least one of: owner name, pet name, record identifier for a prescription, clinic name, authorization status, refill authorization data, reason for requiring compound prescription and combinations thereof. In some embodiments, the simultaneously implemented plurality of instances of the exemplary routines are complex operations as described in at least one of the previous embodiments. In some embodiments, at least 100 complex routines are performed simultaneously per minute.

In some embodiments, the method further includes adding or removing at least one selected pre-programmed element from the exemplary routine after the initiating implementation step and creating a subsequent instance of the exemplary routine in response to a subsequent request to implement the exemplary routine after the adding or removing step, the subsequent instance of the exemplary routine reflecting the addition or removal of the at least one selected pre-programmed element in accordance with the adding or removing step. In some embodiments, one or more data objects are not populated at the time of creating of an instance of the exemplary routine but are populated in order for the instance of the exemplary routine to complete. In some embodiments, logging exists out-of-band.

In some embodiments, the method further includes receiving from a user, trigger instructions defining at least one trigger condition. The creating of an instance of the exemplary routine is based upon a recognition that at least one of the trigger conditions has been met. In some embodiments, at least one of the trigger conditions is a change in data state. In some embodiments, each pre-programmed element operates on one or more of: i) a defined data set and ii) a variable data set. In some embodiments, the method further includes after detecting an error that prevents completion of at least one instance of the pre-programmed elements, receiving an intervention to complete the at least one instance of the pre-programmed element. In some embodiments, the exemplary routine further comprises data object mapping that defines for each exemplary routine the location of data required by one or more pre-programmed elements within the exemplary routine.

In some embodiments, the data object mapping is at least in part defined within the pre-programmed elements. In some embodiments, the method further includes simultaneously implementing one or more instances of an exemplary routine by implementing instances of pre-programmed elements in parallel. In some embodiments, the method further includes sequencing the performance of pre-programmed elements by delaying instructions to implement a pre-programmed element until at least one of another pre-programmed element achieves a predefined state. In some embodiments, the predefined state includes at least one of: i) a completion state; ii) a failure state. In some embodiments, the completion state includes at least a partial completion and the failure state includes failure after a predetermined number of retries.

In some embodiments, at least one pre-programmed element is a long-running pre-programmed element that is programmed to cause other pre-programmed elements within an instance of the exemplary routine in which an instance of the long-running element is included to at least one of: i) pause execution until the long-running element reaches a completion state; ii) delay completion until the long-running element reaches the completion state. In some embodiments, the completion state includes at least one of: i) complete; ii) partial complete; iii) failed to complete; iv) not started and v) delayed. In some embodiments, the method further includes one of completing the instance of the exemplary routine using the state of the respective instances of pre-programmed elements after the instance of the exemplary routine has been created wherein subsequent to the time the instance of the exemplary routine has been created, a change is made to the exemplary routine upon which the instance of the exemplary routine is based; and interrupting the instance of the exemplary routine after receiving a call to interrupt the instance of the exemplary routine based upon call to create a new instance of the exemplary routine using a data site that is also used by the instance of the exemplary routine and the dataset includes a flag set to cause the interruption of the instance of the exemplary routine.

In some embodiments, the method further includes interrupting execution of the instance of the exemplary routine upon receipt of a triggering event. In some embodiments, the method further includes interrupting execution of the instance of the exemplary routine upon receipt of a predetermined number of triggering events including at least one of: i) a network timeout; and ii) a system error. In some embodiments, the triggering event includes one or more of: i) a change to a data record; or ii) a change to pre-programmed element. In some embodiments, each pre-programmed element is fully executable without being directly dependent upon the execution of any other pre-programmed element. In some embodiments, a failure of one instance of one of the pre-programmed elements does not prevent the execution and completion of another instance of the same pre-programmed element. In some embodiments, the instance of the exemplary routine reaches a successful conclusion if all of the pre-programmed elements within the instance of the exemplary routine are completed.

In some embodiments, the method further includes creating one or more additional instances of the exemplary routine, and completing, without intervention, an execution of all of the one or more additional instances of the exemplary routine after detecting an error in the instance of the exemplary routine that prevents the completion of the exemplary routine. In some embodiments, the method further includes after receiving the intervention to complete the at least one instance of the pre-programmed element, and decrementing a retry field to complete execution of the instance of the exemplary routine. In some embodiments, the occurrence of an error that prevents the completion of the instance of the exemplary routine without intervention does not prevent the completion of the one or more additional instances of the exemplary routine.

BRIEF DESCRIPTION OF THE SEVERAL VIEWS OF THE DRAWINGS

The following detailed description of embodiments of the system and method for modular construction of executable programs having self-contained program elements, will be better understood when read in conjunction with the appended drawings of an exemplary embodiment. It should be understood, however, that the invention is not limited to the precise arrangements and instrumentalities shown.

In the drawings:

FIG. 2B is an example of a reaction table according to the entity relationship diagram in FIG. 2A.

FIGS. 6D-6H illustrate an example of an administrator user interface for the creation of a new exemplary routine, in accordance with an exemplary embodiment of the present disclosure.

FIG. 6I illustrates an example of a customer service user interface in accordance with an exemplary embodiment of the present disclosure.

FIG. 14 illustrates an exemplary flowchart for a method of performing a fault tolerant automated sequence of computer implemented tasks, in accordance with an exemplary embodiment of the present disclosure.

DETAILED DESCRIPTION

Figure 1:
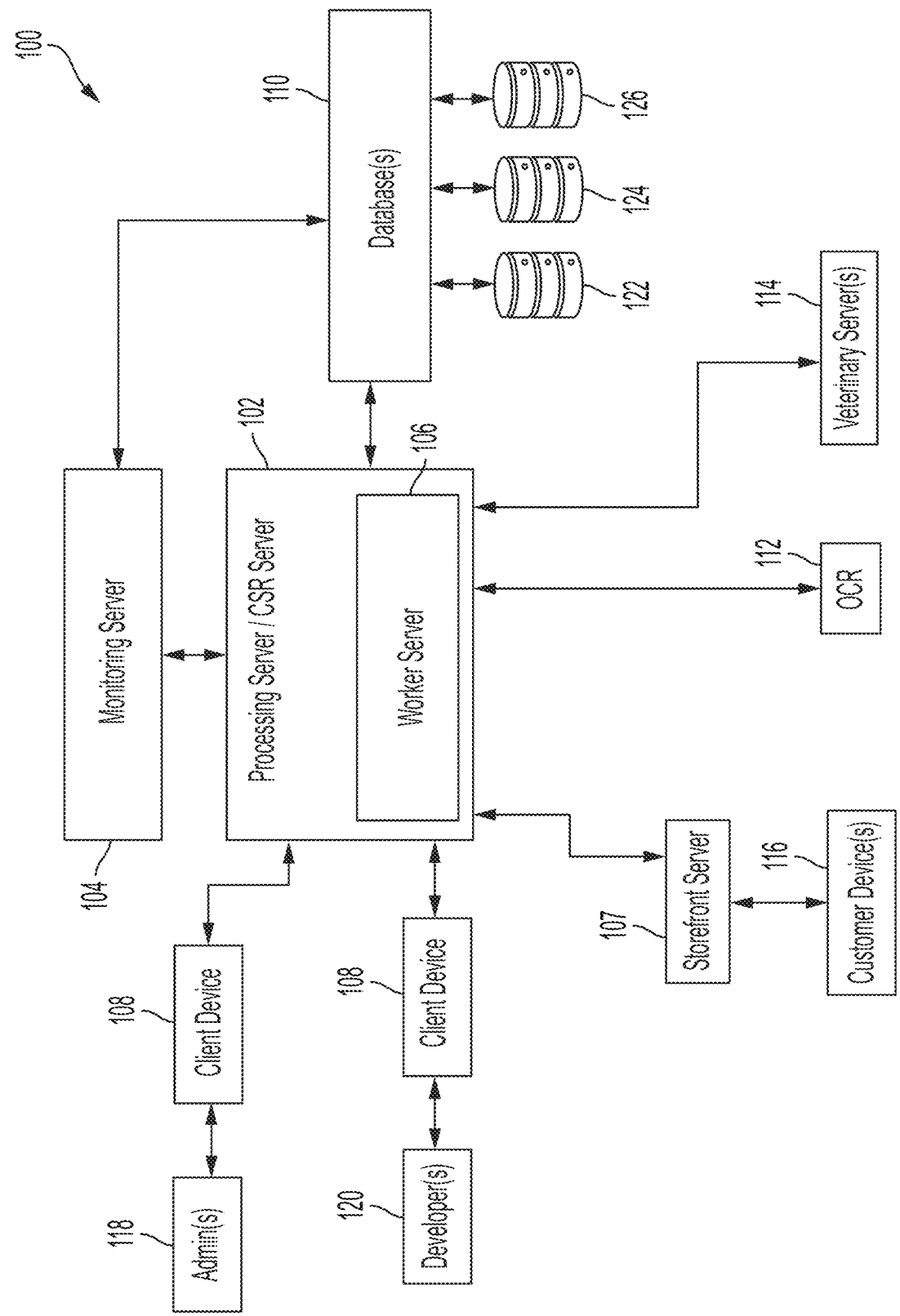
FIG. 1 is a block diagram illustrating an implementation of a process synchronization system, in accordance with an exemplary embodiment of the present disclosure.

Numerous details are described herein in order to provide a thorough understanding of the example embodiments illustrated in the accompanying drawings. However, some embodiments may be practiced without any of the specific details, and the scope of the claims is only limited by those features and aspects specifically recited in the claims. Furthermore, well-known methods, components, and circuits have not been described in exhaustive detail so as not to unnecessarily obscure pertinent aspects of the embodiments described herein.

Some embodiments of the present disclosure provide improvements to generating automated tasks by providing a modular process synchronization system configured to efficiently develop and execute programs having self-contained program elements. The system may be configured to execute and monitor the automated process synchronization programs via two or more servers in communication over a network. Referring to the drawings in detail, wherein like reference numerals indicate like elements throughout, there is shown in FIGS. 1-2 a system for modular construction of executable programs having self-contained program elements, in accordance with an exemplary embodiment of the present disclosure.

In one embodiment, the system for modular construction of executable programs having self-contained program elements 100 includes one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, performs one or more or any combination of the methods or steps disclosed herein.

Referring to FIG. 1, there is shown a block diagram illustrating an implementation of a system for modular construction of executable programs having self-contained program elements, generally designated 100. While some example features are illustrated, various other features have not been illustrated for the sake of brevity and so as not to obscure pertinent aspects of the example embodiments disclosed herein. To that end, as a non-limiting example, the system for modular construction of process synchronization programs 100, referred to herein as system 100, may include one or more networked servers. The one or more networked servers may share any number of logical units. In some embodiments, the one or more networked servers are assigned discrete tasks. For purposes of explaining the invention, reference may be made to a particular server with a particular function. It should be understood that the particular function may be unique to the server or the functionality may be shared by multiple servers.

In one embodiment, system 100 comprises a processing server 102, a monitoring server 104, a worker system 106, one or more client devices 108, and one or more databases 110. The system may further include an optical character recognition (OCR) server 112, one or more veterinarian servers 114, one or more storefront servers 107, and one or more customer devices 116. In one embodiment, the functionality of the processing server 102, monitoring server 104 and worker server 106 is shared by one server or across one or more networked severs. In one embodiment, the functionality of each of the processing server 102, monitoring server 104 and worker server 106 are performed by one more servers that do not overlap in functionality. For example, the one or more servers that provide functionality for the processing server 102 may be different from the one or more servers that provide the functionality of monitoring server 104.

The processing server 102 may be one or more computing servers that provide secure access to a plurality of pre-programmed elements (sometimes referred to herein as "atoms"), one or more of which may be combined into an exemplary routine (sometimes referred to herein as "reactions"). The processing server 102 may be configured to display an administrator facing user interface ("UI"), also referred to as an admin UI, which allows users (e.g., administrators 118, developers 120) to define exemplary routines, and/or request/create new pre-programmed elements. Administrators 118 may be users with little to no computer programming knowledge (e.g., customer service representatives or users having little to no skill in the art of computer programming). Developers 120 may be users with computer programming knowledge necessary to write computer programs which become the pre-programmed elements (e.g., software engineers or users having at least ordinary skill in the art of computer programming). Administrators 118 and developers 120 may access the processing server 102 via client devices 108. Client devices 108 may be operated on any suitable computer device, such as a computer, a laptop computer, a tablet device, a netbook, an internet kiosk, a personal digital assistant, a mobile phone, a smart phone, a gaming device, a computer server, or any other computing device. The processing server 102 may be configured to generate the admin UI such that it is accessible via the internet and viewable by a developer 120 and/or administrator 118 on a respective client device 108.

The processing server 102 may be configured to communicate with one or more servers (e.g., storefront server 107) configured to generate a customer facing UI such that it is accessible via the internet and viewable by a customer on a respective customer device 116. The customer device 116 may be operated on any suitable computer device, such as a computer, a laptop computer, a tablet device, a netbook, an internet kiosk, a personal digital assistant, a mobile phone, a smart phone, a gaming device, a computer server, or any other computing device. The customer facing UI may be configured to allow one or more customers to view and select products for purchase. The products for purchase may have associated data stored in a database in communication with the storefront server 107. In some embodiments, storefront server 107 is in communication with database 110 that stores product data associated with the products for purchase. One or more of the products displayed on the customer facing UI may require authorization in order for a customer to purchase them. For example, a product may be a prescription tick medication for a dog that requires authorization from a veterinarian. The database 110 may store a record indicating whether there is an authorization for a user to purchase a specific product displayed on the customer facing UI. The processing server 102 and/or storefront server 107 may be configured to query database 110 to determine if a prescription authorization for the requested product exists. The database may store customer information such as: customer name, address, phone number, pet information, veterinary clinics associated with the pets owned by the customer, and prescription information.

The processing server 102 may be configured to communicate with one or more databases (e.g., database 110) to receive and transmit data relating to pre-programmed elements, and/or exemplary routines. Database 110 may include a relational database (see FIG. 2). In some embodiments, database 110 may include a non-relational database. Database 110 may store data related to a plurality of pre-programmed elements. A pre-programmed element may be an element of computer executable code written by a programmer (e.g., developer 120, software engineer, computer scientist). A pre-programmed element may be an independently executable self-contained unit of computer code configured to perform a specific task (e.g., send email to customer, process order refund, cancel order shipping). Independently executable refers to the configuration of each pre-programmed element to complete execution without requiring an output from any other pre-programmed element which has executed so long as any data objects required for the pre-programmed element are known. The data related to the pre-programmed elements may include a unique identifier which identifies each pre-programmed element, and the executable self-contained unit of computer code.

The database 110 may store data related to exemplary routines associated with one or more pre-programmed elements that correspond to tasks required to accomplish a certain objective. An exemplary routine may be a grouping of pre-programmed elements having a sequence that defines the order in which the pre-programmed elements execute. For example, an objective may be to process the termination of and cancel a pending order for a product that was placed through a customer portal. To fully process the termination of a pending order the system 100 may implement tasks for: communication related to the customer account associated with the order, rigorous financial processing steps, shipping notices and inventory management. Specific automated tasks may include: transmission of electronic notification related to customer account that the order has been cancelled, processing of refund request associated with the customer account, termination of shipping order and, if necessary, returning a product to inventory or indicating in an inventory tracking system that the product is available for sale in connection with a new order. In this example, the exemplary routine would include pre-programmed elements that have executable code capable of handling the above-mentioned tasks and define the order in which the pre-programmed elements are executed. Further to this example, the sequence of execution may be to cancel shipping of the product to the customer, process a refund to the customer, and email the customer a notification that the order cancellation has been processed. It will be understood though, that exemplary routines may include different pre-programmed elements and/or define different sequences of execution for the pre-programmed elements.

The pre-programmed elements may be associated with one or more exemplary routines. For example, the send email pre-programmed element may be included in a plurality of different exemplary routines (e.g., order cancellation requests, requests for additional customer information, notifications for a change in quantity of an ordered product). Data stored in database 110 relating to an exemplary routine may include a unique identifier for the exemplary routine, the sequence in which pre-programmed elements are to be executed, and a listing of the pre-programmed elements that are included in the exemplary routine. In some instances, an exemplary routine may include two or more of the same pre-programmed elements. For example, an exemplary routine X may include pre-programmed elements A, B, and C and include A, B, C, A as the order of execution. In some instances, an exemplary routine may include two or more pre-programmed elements having the same sequence value. For example, an exemplary routine may include pre-programmed elements A, B, C, and D and a sequence that defines the order of execution to be A, then BC, then D where element A executes, then elements B and C execute in parallel (e.g., initiating at the same time or approximately the same time or overlapping execution), then element D executes.

The database 110 may also store data required for execution of one or more of the pre-programmed elements. The database 110 may store data associated with customer records, customer interactions, and/or clinics (e.g., veterinary clinics, veterinarians). Customer record data may include data relating to the customer and/or an account owned by the customer and stored in database 110 (e.g., unique customer ID, customer name, email address, phone number, shipping address, and pet(s) owned by the customer). Customer interaction data may include data relating to one or more interactions of the customer with the storefront server 107 (e.g., unique identifiers associated with orders for products placed by the customer, products ordered by the customer, shipping address, payment method, order quantity, order status, payment status, and shipping method). Clinic data may include data relating to one or more clinics associated with a customer, processing server 102, and/or storefront server 103 (e.g., a veterinarian associated with a customer's pet, the veterinarians contact information, and the veterinarian's veterinary clinic). Depending on the pre-programmed element, some of said data may be required to execute said pre-programmed element. For example, a pre-programmed element configured to email a customer with a notification may require customer records to determine the customer's email address. Similarly, a pre-programmed element configured to refund payment of a cancelled order may require data associated with an order number and payment method. It will be understood that the database 110, or another database in communication with database 110 and/or processing server 102 may store data required for execution of the pre-programmed elements.

The processing server 102 may be configured to receive a request for execution of one or more pre-programmed elements. The request for execution of one or more pre-programmed elements may be in response to an event, or occurrence, for which a resolution is sought. The event may be referred to as a triggering event or an incident herein. For example, an incident may be a customer requesting cancellation of an order. In order to resolve the customer's order cancellation incident, one or more tasks may be executed, preferably in a certain order, in order to resolve the order cancellation incident. The one or more tasks may correspond to one or more of the pre-programmed elements which may be included in an exemplary routine. The request for execution of the one or more pre-programmed elements may include an indication as to the exemplary routine associated with the one or more pre-programmed elements. The processing server 102 may transmit the request for execution of the one or more pre-programmed elements in response to an input from an administrator 118 and/or a developer 120. The input from the administrator 118 and/or developer 120 may be received on an associated client device 108 displaying the admin UI. For example, an administrator 118 may receive communication (e.g., email, phone call, a message through an online communication platform) from a customer that wishes to cancel an order. The administrator 118 may, via a client device 108, access the processing server 102 which transmits the admin UI for display on client device 108. The administrator 118 may then, after locating the order in which the user wishes to cancel, provide an input, via the client device 108, at a displayed icon on the admin UI to cancel the order (e.g., a 'cancel order' button). Additional non-limiting examples of incidents which trigger execution of one or more pre-programmed elements may include a request by a veterinary clinic to switch from paper (e.g., fax) notifications to electronic notifications (e.g., email), a request to email all veterinarians associated with a specific veterinary clinic the number of pending prescriptions for their review, and a notification sent to a customer to verify a duplicate order to ensure the duplicate order was not accidental.

The processing server 102 may be configured to communicate with database 110 to create and store instances of one or more exemplary routines and/or one or more instances of pre-programmed elements for which execution is requested. An instance of an exemplary routine (sometimes referred to as a "molecule" herein) may refer to a version of the exemplary routine stored in database 110. In one embodiment, the version of the exemplary routine that makes up the instance is based on the configuration of the exemplary routine at the time the instance was created. That version of the exemplary routine may differ from a later created instance of the exemplary routine. For example, an aspect of one of the pre-programmed elements may be changed between the creation of a first instance and a second instance of the same exemplary routine, where the second instance is created later than the first instance. In one embodiment both instances (e.g., the first and second instance) of the exemplary routine are stored in the database and may be executed according to their respective configurations at the time they were created. In some embodiments, the aspect of the exemplary routine that is changed includes one or more of: i) the substitution of one pre-programmed element for another pre-programmed element; ii) the addition of a pre-programmed element; iii) the elimination of a pre-programmed element; iv) a change to the sequence of performance of the pre-programmed element; v) a new sequence for a new set of pre-programmed elements; or vi) a combination of two or more of the foregoing.

In one embodiment, a first instance of an exemplary routine X is created at a time T1 and may correspond to the configuration of the exemplary routine X at time T1. Exemplary routine X may be modified at a second time T2 after T1 such that a pre-programmed element is added or removed from the exemplary routine. A second instance of exemplary routine X is created on or after the second time T2 and may include the configuration corresponding to the modification made at T2. Both the first instance and second instance of exemplary routine X may be stored in database 110 for processing while the first instance represents the configuration of exemplary routine X at time T1 and the second instance represents the configuration of exemplary routine X after modification (e.g. on or after time T2). The configuration of an exemplary routine at the time an instance is created may include data such as an identifier for the exemplary routine (e.g., a name for the exemplary routine, a unique identifier), a listing of pre-programmed elements included in the exemplary routine, and the sequence of execution for the pre-programmed elements.

In some embodiments, the instance of the exemplary routine includes a version of the exemplary routine that includes one or more pointers to executable code (e.g., executable code associated with pre-programmed elements included in the exemplary routine). In some embodiments, the instance of the exemplary routine contains no executable code and includes, instead, pointers to executable code. In one embodiment, when the code associated with a pre-programmed element is updated any instance of an exemplary routine that has not yet run, will execute from the updated code when the instance is executed. In one alternative embodiment, the instance of the exemplary routine includes executable code that does not execute via a pointer and does not therefore run updated code if a relevant pre-programmed element is updated after the instance is created.

In one embodiment, database 110 may store exemplary routines and instances of exemplary routines. For example, database 110 may store an exemplary routine X which is for handling an order cancellation request. The database 110 may store a configuration of exemplary routine X (e.g., data relating to the exemplary routine). The configuration may include a unique identifier for the exemplary routine, pre-programmed elements included in the exemplary routine as they exist at the time the instance is created, and the associated sequence of execution as that sequence is defined at the time the instance is created. In some embodiments, an instance of the exemplary routine is a version of the exemplary routine which may be stored as a record in database 110 separate from the exemplary routine to which it corresponds. For example, exemplary routine X is stored separately from the instance of exemplary routine X in database 110. There may be a plurality of instances of exemplary routines stored in database 110. For example, in some instances there may be two or more instances of exemplary routine X stored in database 110 and one or more instances of different exemplary routines stored in database 110. In some embodiments, there may be ten or more, fifty or more, one hundred or more, or more than a hundred instances of exemplary routines stored in database 110. Instances of exemplary routines stored in database 110 may include multiple instances of the same exemplary routine, instances of different exemplary routines, or any combination thereof.

An instance of one or more pre-programmed elements may refer to a copy of the data corresponding to the pre-programmed element stored in database 110. For example, database 110 may store a pre-programmed element A that is for sending an email notification. The data associated with pre-programmed element A includes the unique identifier and a pointer to the computer code to be executed. An instance of pre-programmed element A is a copy of said data including the unique identifier and a pointer to the computer code to be executed corresponding to pre-programmed element A. The instance of the pre-programmed element may be stored as a record in database 110, separate from the pre-programmed element it corresponds to. For example, pre-programmed element A is stored separately from the instance of pre-programmed element A in database 110. There may be a plurality of instances of a pre-programmed element stored in database 110. For example, in some embodiments, there may be two or more instances of pre-programmed element A stored in database 110. In some embodiments, there may be ten or more, fifty or more, one hundred or more, or more than a hundred instances of the same pre-programmed element stored in database 110. In some embodiments, two or more databases are used to store pre-programmed elements and instances of the pre-programmed elements respectively. Database 110 may include an elements database 122, routines database 124 and instances database 126. The elements database 122 may be configured to store the pre-programmed elements created as described above. The routines database 126 may be configured to store the exemplary routines created as described above. The instances database 128 may be configured to store instances of pre-programmed elements, and exemplary routines created as described above. An instance of an exemplary routine and/or an instance of a pre-programmed element may be a version of the exemplary routine and/or pre-programmed element that is applicable at the point in time in which the instance was created.

The processing server 102 may be configured to create an entry in database 110 for an instance of an exemplary routine for which execution is requested. The processing server 102 may include executable code, that when executed, causes the database 110 to create one or more rows including data for the instance of the exemplary routine, and instances of the pre-programmed elements included in the exemplary routine. The processing server 102 may be configured to cause database 110 to create data entries for data related to the incident which triggered the creation of the instance of the exemplary routine and/or data entries required for execution of instances of pre-programmed elements. For example, database 110 may store, for each instance of an exemplary routine, incident data which may correspond to data for a customer interaction record, contact data corresponding to customer and/or veterinarian contact records, and/or org data corresponding to veterinarian clinic records, shelter records, or the like.

Figure 2A:
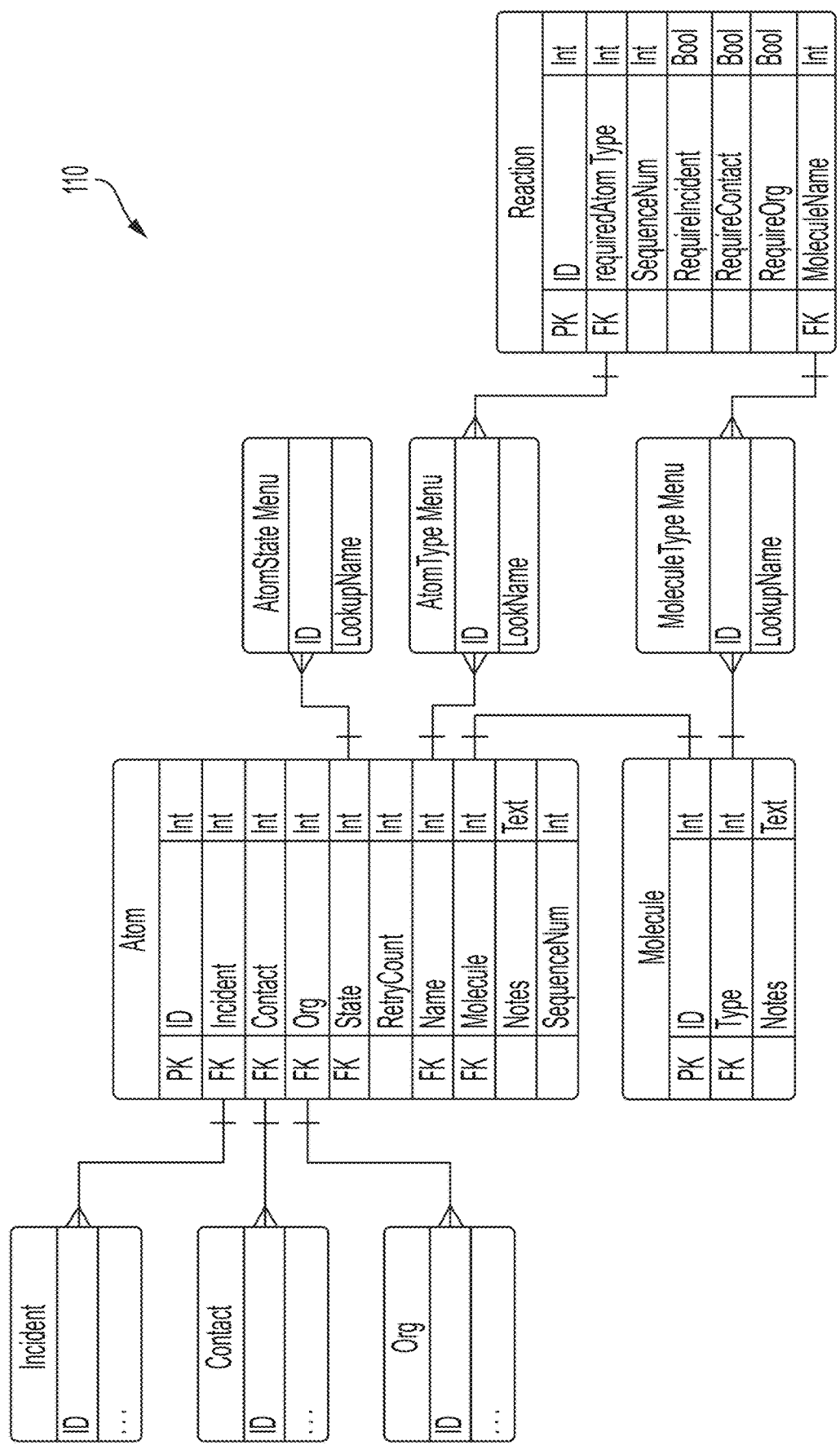
FIG. 2A is an entity relationship diagram illustrating an implementation of the database of FIG. 1.

Referring to FIG. 2A, there is shown an entity relationship (ER) diagram for database 110 in accordance with an exemplary embodiment of the invention. The ER diagram in FIG. 2 may relate to how instances of exemplary routines are associated with corresponding exemplary routines, instances of pre-programmed elements, incident data, and other data required for the execution of the instance of the exemplary routine. Database 110 may store data associated with incidents, contacts, orgs, pre-programmed elements, exemplary routines, and instances of exemplary routines in one or more tables. The database 110 may include an incident table, contact table, and org table for storing data associated with incidents, contacts, and organizations respectively. Database 110 may include an atom table, atom state menu table, and atom type table for storing data related to pre-programmed elements. Database 110 may include a molecule and molecule type menu tables for storing data related to instances of exemplary routines. Database 110 may include a reactions table for storing data related to exemplary routines.

Data associated with an instance of a pre-programmed element may include: a unique ID, incident, contact, org, state, retry count, name, molecule, notes, and/or sequence number data entries. The unique ID may be a unique identifier which is specific to the instance of the pre-programmed element. The incident entry may be an optional foreign key that links the instance of the pre-programmed element and the incident which triggered creation of the instance of the exemplary routine stored in a separate table in database 110. The contact entry may be an optional foreign key that links the instance of the pre-programmed element to customer and/or veterinarian information stored in a separate table on database 110. The org entry may be an optional foreign key that links the instance of the pre-programmed element to veterinarian clinic, shelter information stored in a separate table on database 110. The state entry may include an indication of the status (e.g., the state) of the pre-programmed element (e.g., pending, cancelled, failed, completed, locked). The state may be an integer value indicating the status of the instance of the pre-programmed element (e.g., 0=pending, 1=cancelled, 2=failed, 3=complete, 4=locked). The state may alternatively be a text value corresponding to the status of the pre-programmed element. The retry count entry may correspond to a number of times execution of an instance of the pre-programmed element has been attempted as discussed in more detail below. The name entry may be a human readable name of the pre-programmed element and may be a foreign key that links the instance of the pre-programmed element to the corresponding pre-programmed element stored in a separate table in database 110. The molecule entry may be a foreign key that links the instance of the pre-programmed element to the corresponding instance of the exemplary routine. The notes entry may be a free form field that may be used to store structured data required for execution. For example, the notes entry may include a JSON formatting array storing one or more identifiers required for execution of one or more pre-programmed elements. The sequence number entry may correspond to a sequence number for the instance of the pre-programmed element that is copied from the exemplary routine during creation of the instance of the exemplary routine. Sequence numbers created in this manner and stored as a data entry in the instance of the pre-programmed element may allow execution of the pre-programmed element as defined by the exemplary routine at the time the instance of the exemplary routine is created. Put another way, by storing the sequence number during creation of an instance of the exemplary routine, the pre-programmed element will execute according to the sequence defined by the exemplary routine even if the exemplary routine is modified during execution of the instance of the exemplary routine, as described in more detail below.

Database 110 may include one or more tables for storing information related to instances of the exemplary routines. Data associated with instances of exemplary routines may include a unique identifier, a type, and notes data entries. The unique identifier may be a private key that is unique to the instance of the exemplary routine and may link the instance of the exemplary routine to instances of corresponding pre-programmed elements (e.g., the unique identifier data entry and molecule data entry). The type data entry may be a foreign key that defines a many-to-many relationship between the instance of the exemplary routine and the exemplary routine. The many-to-many relationship may be established via a table (e.g., the MoleculeType Menu) that links the table storing data for the instance of the exemplary routine and the table storing data for the exemplary routine. The notes data entry may be a free form field to store data. In some embodiments, notes data in the molecule table includes structured data that is required or useful for some implementations.

Database 110 may include one or more tables (e.g., the reaction table) for storing information related to exemplary routines. Data associated with exemplary routines may include a unique identifier, required atom type, sequence number, require incident, require contact, require org, and/or molecule name data entries. The unique identifier may be a private key which is unique to the exemplary routine. The required atom type data entry may be a foreign key corresponding to one or more pre-programmed elements required for execution. The sequence number data entry may include the order of the execution for the pre-programmed elements included in the exemplary routine. The require incident data entry may include an indication as to whether incident information must be present in database 110 for execution of the instance of a pre-programmed element included in the exemplary routine. In one exemplary embodiment, the require incident data entry may be specific to an instance of a pre-programmed element. For example, the require incident data entry may be "yes" for an instance of pre-programmed element A and "no" for an instance of pre-programmed element B. In another exemplary embodiment, the require incident data entry may not be specific to an instance of a pre-programmed element. The require contact data entry may include an indication as to whether contact information must be present in database 110 for execution of the instance of a pre-programmed element included in the exemplary routine. In one exemplary embodiment, the require contact data entry is specific to an instance of a pre-programmed element. In another exemplary routine, the require contact data entry is not specific to an instance of a pre-programmed element. The require org data entry may include an indication as to whether organization data (e.g., veterinary clinic data, shelter data) must be present in database 110 for execution of the instance of a pre-programmed element included in the exemplary routine. In one exemplary embodiment, the require org data entry may be specific to an instance of a pre-programmed element. In another exemplary embodiment, the require org data entry may not be specific to an instance of a pre-programmed element. The molecule name data entry may be a foreign key which defines the instance of the exemplary routine that a pre-programmed element will be included in.

Referring to FIG. 2B there is shown an example of a reaction table storing information related to an exemplary routine "cancelpetscriptionrelease". Each row in this example reaction table corresponds to a pre-programmed element included in the exemplary routine and/or an instance of the pre-programmed elements included in an instance of the exemplary routine. The reaction table shown here includes the pre-programmed elements and corresponding sequences defined by the exemplary routine. In this example, the exemplary routine includes four pre-programmed elements: "cancelpetscriptionrelease", "cancelpetscriptionreleasesendemail", and two "orgisDigital" pre-programmed elements. Each pre-programmed element may include a unique ID associated with pre-programmed element. In some embodiments the unique ID is associated with an instance of the pre-programmed element (e.g., ID values 16 and 17 correspond to different instances of pre-programmed element "orgsIsDigital"). Each pre-programmed element may include an indication of what information is required in order for the pre-programmed element to execute. For example, pre-programmed element "cancelpetscriptionrelease" requires incident information but does not require contact or organizational information in order to execute. Each pre-programmed element may include a sequence data associated with the sequence of execution as defined by the exemplary routine. For example, "petscriptionrelease" and one instance of "orgsIsDigital" have a sequence value of 1 indicating that instances of these two pre-programmed elements should be executed in parallel. It will be understood that the reaction table shown in FIG. 2B is an example and that in practice the reaction table may store a plurality of entries associated with different instances of exemplary routines each including one or more instances of pre-programmed elements.

The database 110 may store a table associated with the type of pre-programmed element (e.g., the AtomType Menu in FIG. 2) for relating an instance of a pre-programmed element with the executable code for the corresponding pre-programmed element. In some embodiments, storing the executable code for a pre-programmed element separate from the instance of said pre-programmed element may allow the system 102 to maintain referential integrity within database 110. In some embodiments, storing the executable code for the pre-programmed element separate from the instance of said pre-programmed element may allow an exemplary routine to be modified without affecting an instance of said exemplary routine which is currently being executed.

The database 110 may store a plurality of instances of different pre-programmed elements. For example, the database 110 may store a record of three instances of pre-programmed element A, five records of pre-programmed element B, and 10 records of pre-programmed element C. It will be understood that the database 110 may store any number or combination of instances of pre-programmed elements. The database 110 may include a record of all pre-programmed elements with a pending status.

The processing server 102 may be configured to transmit a request to database 110 to create and store an instance of each pre-programmed element in an exemplary routine in database 110. The request from processing server 102 to database 110 to store said instances may be in response to an input and/or request received from a client device 108. The input and/or request from client device 108 may correspond to an input from an administrator 118 or developer 120 who wishes to cause system 100 to perform a series of tasks. For example, an administrator 118 may provide an input on client device 108 that is displaying an admin UI to request cancellation of an order for a product (e.g., a press of a button displayed on admin UI corresponding to cancelling an order). The order cancellation input may cause processing server 102 to transmit a request to database 110 to create an instance of each pre-programmed element included in an exemplary routine for order cancellation. As described above, this exemplary routine may include pre-programmed elements for email notifications, a refund of the currency to a customer that placed the order, and a cancellation of any pending shipment of the product to the customer. In this example, an instance of each of these pre-programmed elements is created and stored in database 110 for execution. Each instance of pre-programmed elements included in the exemplary routine may initially be stored in database 110 with a pending status indicator.

The processing server 102 and monitoring server 104 may be configured to determine the order in which instances of pending pre-programmed elements should be executed and/or to execute said instances. The monitoring server 104 may be configured to transmit a request for a list of all pending instances of pre-programmed elements to processing server 102. The processing server 102 may be configured to determine, based on the data associated with instances of the pre-programmed elements, the order in which the pre-programmed elements should be executed. For example, the processing server 102 may be configured to determine that an instance of pre-programmed element B should not be executed until an instance of pre-programmed element A is executed. The processing server 102 may be configured to determine the order in which instances of pre-programmed elements are to be executed as defined by an instance of the exemplary routine. For example, an instance of a first exemplary routine may include instances of pre-programmed elements A-D having a defined sequence (e.g., element A executes before element B that executes before element C that executes before element D). For example, an instance of an exemplary routine may have three instances of pre-programmed elements which have not executed and the processing server 102 may determine which of those instances needs to be executed next as defined by the sequence.

The processing server 102 may be configured to determine a portion of instances of pre-programmed elements for execution from the record of all pending pre-programmed elements stored in database 110. For example, database 110 may have stored, at a point in time, one hundred instances of pre-programmed elements having a pending status. The processing server 102 may determine that twenty of the one hundred instances of pre-programmed elements need to be executed. The processing server 102 may determine the portion of pre-programmed elements for execution based on corresponding instances of exemplary routines. For example, if database 110 has stored therein one hundred instances of pre-programmed elements, those instances may correspond to twenty instances of exemplary routines. Each instance an of exemplary routine including the sequence of execution for corresponding instances of pre-programmed elements which are stored in database 110. The processing server 102 may determine where in the sequence of execution, each instance of an exemplary routine is currently at (e.g., a first exemplary routine has not started, a second exemplary routine has executed the second instance of a pre-programmed element in its sequence). Based on the current sequence of execution, the processing server 102 may determine which instances of pre-programmed elements need to be executed next. For example, if there are twenty instances of exemplary routines, each including five instances of pre-programmed elements, none of which have been executed yet, the processing server 102 is configured to determine that the instance of a pre-programmed element corresponding to the first pre-programmed element in the sequence defined by the corresponding instance of the exemplary routine needs to be executed.

In one embodiment, system 100 also includes logical units (LUs) that includes one or more of a monitor LU, a processor LU and a worker LU. In one embodiment, the monitor LU is a logical unit that initiates executions and monitors progress of various activities on system 100. For example, the monitor LU may include an AWS Step-Function, an AWS Lambda, and/or associated monitoring and alerting. In one embodiment, the processor LU includes several code-classes used to i) collect data on pending executions, ii) execute pending tasks, iii) communicate information back to the monitor unit and iv) combinations thereof. The processor LU may include files (such as plain-text files) that may be executed by one or more of the servers for rendering on a browser. In some embodiments, the monitor LU includes a cron_runner function configured to request pending instances of pre-programmed elements and receive requests for execution of instances of pre-programmed elements. In some embodiments, the monitor LU includes a parallel_process_atoms function configured to handle the execution of code corresponding to the pre-programmed elements as well as retrieve a list of pending instances of pre-programmed elements to be executed. In some embodiments, the processing LU includes a molecule_utilities function configured to create entries in database 110 for new pre-programmed elements and cancel pending instances of exemplary routines. In an exemplary routine, the molecule_utilities functions is configured to handle all entries and deletions from database 110 relating to exemplary routines, pre-programmed elements, and/or instances thereof. In one embodiment, the worker LU includes a body of code used to complete the actions defined for a requested pre-programmed element. For example, the worker LU may include code for completing actions defined by pre-programmed elements such as: processsendorgstatustokyrios, clinicprefupdateatom and processcancelRxOrder-InPetcriptions. In one embodiment, the worker LU includes one or more private methods within the one or more files of the processor LU and can call out to other functions or classes.

In some embodiments, each of the monitor LU, processor LU and worker LU are associated with and executed by a dedicated server. In some embodiments, one or more servers are configured to execute one or more of the LUs. In other embodiments, the LUs are shared across two or more servers. The monitoring server 104 may be one or more computing servers that are configured to initiate the execution of and monitor the status of instances of pre-programmed elements. The monitoring server 104 may be configured to communicate with database 110 to request and receive a record of all pending pre-programmed elements for which execution is requested. The monitoring server 104 may be configured to request the record of all pending pre-programmed elements at a pre-defined interval. In some embodiments, the pre-defined interval is one minute. In some embodiments, the pre-defined interval is about 30 seconds, about 60 seconds, about 90 seconds, about 120 seconds, about 150 seconds or about 180 seconds.

The processing server 102 may create a list of all instances of pre-programmed elements to be executed next in sequences defined by the instances of exemplary routines and transmit the list to the monitoring server 104. The monitoring server 104 may be configured to assign, based on the list received from the processing server 102, instances of pre-programmed elements to one or more sets of instances of pre-programmed elements for parallel execution. For example, the monitoring server 104 may receive a list of a thousand instances of pre-programmed elements from processing server 102. The monitoring server 104 may then determine that one set for parallel execution may include ten instances of the thousand instances received and another set may include twenty instances and so on. The monitoring server 104 may be configured to initiate execution of one or more instances pre-programmed elements. The monitoring server 104 may be configured to initiate execution of one or more instances pre-programmed elements identified for execution by processing server 102, as described above. The monitoring server 104 may be configured to iterate through the determined sets for parallel execution and transmit said sets to the processing server 102 to initiate execution of the instances of pre-programmed elements included in said set. For example, the monitoring server 104 may, after determining the sets for parallel execution, transmit the sets to the processing server 102 for execution. In this manner, the monitoring server 104 may initiate execution of instances of pre-programmed elements and the processing server 102 may perform the execution of the instances. In one exemplary embodiment, each iteration through the determined sets may correspond to a predetermined interval (e.g., interval defined in step 502 of method 500 discussed below). In other embodiments, the monitoring server 104 is configured to iterate through the determined sets for parallel execution, initiate execution of the instances of pre-programmed elements and perform execution of the instances.

As mentioned above, the monitoring server 104 may be configured to initiate execution of instances of two or more pre-programmed elements in parallel. The two or more instances pre-programmed elements may be two or more instances of the same pre-programmed element. For example, the two or more instances of pre-programmed elements may be two or more instances of pre-programmed element A. In some embodiments, the two or more instances of pre-programmed elements may be two or more instances of different pre-programmed elements. For example, the two or more instances of pre-programmed elements may be an instance of pre-programmed element A and an instance of pre-programmed element B. In some embodiments, the two or more instances of pre-programmed elements may be a combination of instances of the same pre-programmed elements and different pre-programmed elements. For example, the two or more instances may be two instances of pre-programmed element A, an instance of pre-programmed element B, and two instances of pre-programmed element C. The instances of two or more pre-programmed elements executed in parallel may be associated with different instances of exemplary routines. For example, an instance of element A may be associated with an instance of a first exemplary routine and an instance of element B may be associated with an instance of a second exemplary routine.

The processing server 102 may be configured to monitor whether an instance of a pre-programmed element fails to execute. For example, the processing server 102 may monitor the execution of an instance of pre-programmed element A and determine that the instance of pre-programmed element A failed or succeeded to execute. In the event that an instance of a pre-programmed element fails to execute, the processing server 102 may be configured to retry execution of the failed instance of the pre-programmed element. The processing server 102 may be configured to retry execution of an instance of a pre-programmed element a predetermined number of times before ceasing to retry execution of the instance of the pre-programmed element. The processing server 102 may be configured to retry execution one time, two times, three times, four times, five times, six times, seven times, or more than seven times before ceasing to proceed to another retry.

The monitoring server 104 may be configured to validate that execution of instances of pre-programmed elements do not proceed past a predetermined time threshold, that the processing server 102 does not become unresponsive, and/or that a predetermined number of instances of pre-programmed elements are executed in parallel. The monitoring server 104 may be configured to transmit an alert notification to an administrator 118 and/or developer 120 if the processing server 102 becomes unresponsive. The monitoring server 104 may be configured to monitor the amount of time that an instance of a pre-programmed element is taking to execute. For example, the monitoring server 104 may be configured to determine that an instance of pre-programmed element A has taken a minute to execute. The monitoring server 104 may be configured to be in communication with processing server 102 to transmit information corresponding to the status of instances of pre-programmed elements. The monitoring server 104 may transmit to the processing server 102 a list of the instances of pre-programmed elements which have failed to execute, have succeeded to execute, and/or that are currently executing.

The processing server 102 may be configured to monitor the monitoring server 104 to monitor instances of pre-programmed elements that are being executed and monitor any buildup of pending instances of pre-programmed elements that need to be executed. In this manner, the functionality of the system 100 described herein is split between at least two servers (e.g., processing server 102 and monitoring server 104). In one embodiment, splitting functionality between processing server 102 and monitoring server 104 enables redundant monitoring functionality such that processing server 102 may monitor monitoring server 104 and vise versa to identify whether there is a server failure at either the processing server 102 or monitoring server 104 (e.g., failure to execute pre-programmed elements, network connection issues). In the event instances of pre-programmed elements are not fully executed, corrective action may be taken to ensure errors in execution of pre-programmed elements does not cause a halt in execution of other instances of pre-programmed elements.

The processing server 102 may include a worker system 106 which may be configured to execute instances of pre-programmed elements. For example, worker system 106 may include a collection of computer executable code (e.g., PUP scripts) that performs the functions of sending requests to external system for order cancellation, emailing, updating database entries, and/or synchronizing prescription data between different servers.

The processing server 102 may, during execution of an instance of an exemplary routine, be configured to detect the absence of data needed to complete the execution of the instance of the exemplary routine. The data needed to complete the execution of the instance of the exemplary routine may be, for example, a prescription authorization for a product which a customer has placed an order for. The processing server 102 may, in response to the absence of the data needed, be configured to automatically transmit a request for the data to an entity. The entity may be an authorizing entity. For example, the processing server 102 may transmit an authorization form for a prescription medicine to a veterinarian, a clinic, or some other authorizing entity. The entity may receive the request for data (e.g., a prescription authorization form) and enter the requested data. The entity may transmit back to the processing server the requested data, where the data is in an electronic format and/or where the data was handwritten. For example, the authorizing entity may receive a prescription authorization form that the entity may then fill out with handwritten information, information typed into the form via a customer device 116, or a combination of both. The prescription authorization form containing the requested data may be scanned into an electronic format which is then sent to processing server 102 or it may be sent via fax, or mail.

The processing server 102 may be configured to automatically populate data corresponding to the data received from the entity. The processing server 102 may be configured to store the data received from the entity in a database (e.g., database 110). In some instances, the processing server 102 may receive documentation including information to be stored in a database (e.g., database 110) that requires additional processing before the information can be stored in said database. For example, a fax of the prescription authorization form is sent from a veterinarian, or veterinarian clinic, and received by processing server 102. For this reason, the processing server 102 may be configured to communicate with an optical character recognition (OCR) server 112. The OCR server 112 may be configured to receive one or more documents from processing server 102 for which optical character recognition is required. For example, processing server 102 transmits the prescription authorization form, or a copy thereof, to OCR server 112. The OCR server 112 may be configured to receive the documentation (e.g., the prescription authorization) and perform optical character recognition to create a datafile containing optical character recognition data associated with the documentation. The OCR server 112 may transmit the created datafile to processing server 102. The processing server 102 may be configured to automatically store the datafile received from OCR server 112 in a database (e.g., database 110). The processing server 102 may be configured to apply regular expression matching logic to the datafile received from OCR server 112 to identify data associated with at least one of: owner name, pet name, record identifier for a prescription, clinic name, authorization status, refill authorization data, and reason for requiring compound prescriptions, or any combination thereof.

Figure 3:
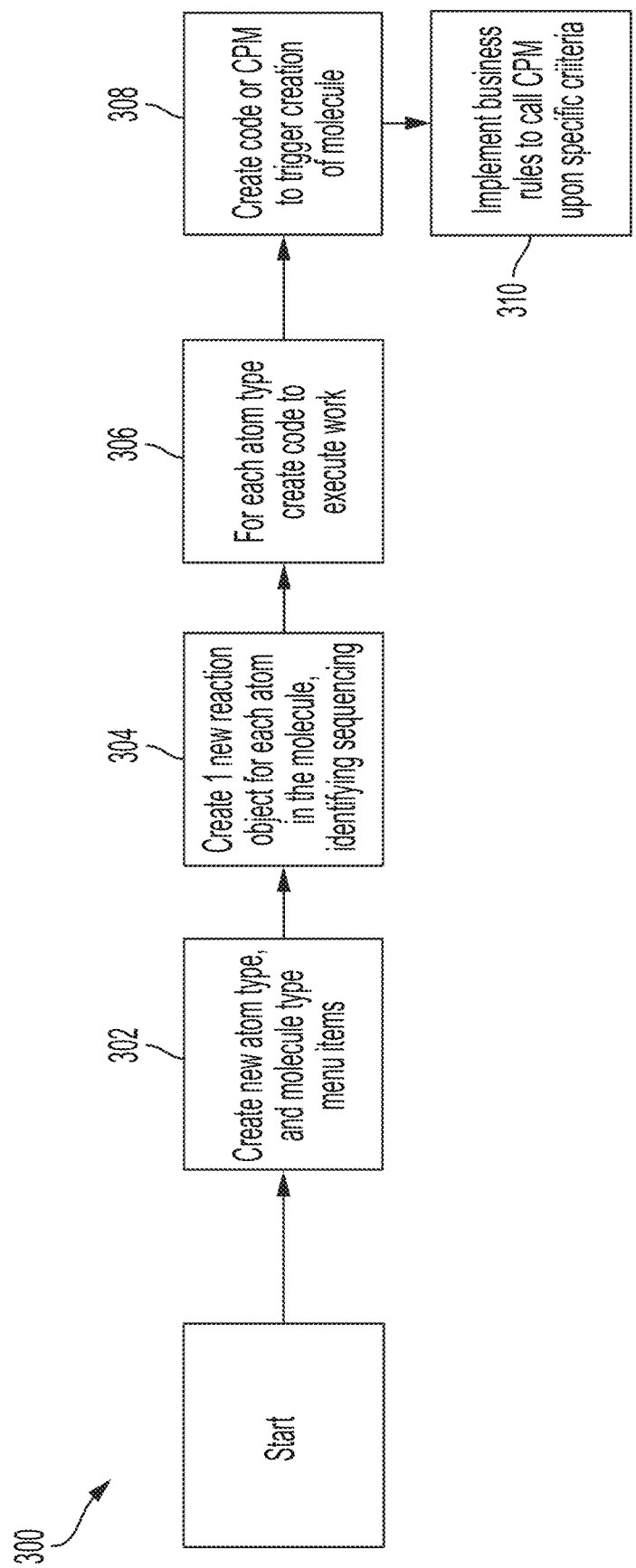
FIG. 3 illustrates an exemplary flow chart for a method of creating an exemplary routine in accordance with an embodiment of the present disclosure

A user (e.g., administrator 118, developer 120) may desire to create an exemplary routine in response to a business process for which system 100 has no automated process in place to accomplish. The business process may be related to a customer service need such as the editing or cancelling of an order. Referring to FIG. 3, there is illustrated an exemplary flow chart for a method of creating an exemplary pre-programmed routine in accordance with an embodiment of the present disclosure. The method 300 may include the step 302 of creating one or more new pre-programmed element types and/or a new instance of an exemplary routine. A pre-programmed element type may refer to a name given to a pre-programmed element (e.g., rxmTransmission, cancelpetscriptionrelease). The method 300 may include the step 304 of creating a new exemplary routine for each pre-programmed element included in the instance of the exemplary routine. The new exemplary routine may define the sequence of execution for the pre-programmed elements included in the instance of the exemplary routine. The method 300 may include the step 306 of creating computer executable code for each pre-programmed element type created in step 302. The creation of computer executable code may be accomplished by a developer 120.

The method 300 may include the step 308 of creating computer executable code or a custom process module (CPM) that is configured to trigger creation of the instance of the exemplary routine. The method 300 may include the step 310 of implementing business rules to call the code or CPM created in step 308 when pre-defined criteria are met. For example, at step 310 an administrator may define events that trigger the creation of an instance of an exemplary routine for execution of the instance of the exemplary routine to complete the relevant task (e.g., processing a return to inventory after a product order has been canceled).

Figure 4:
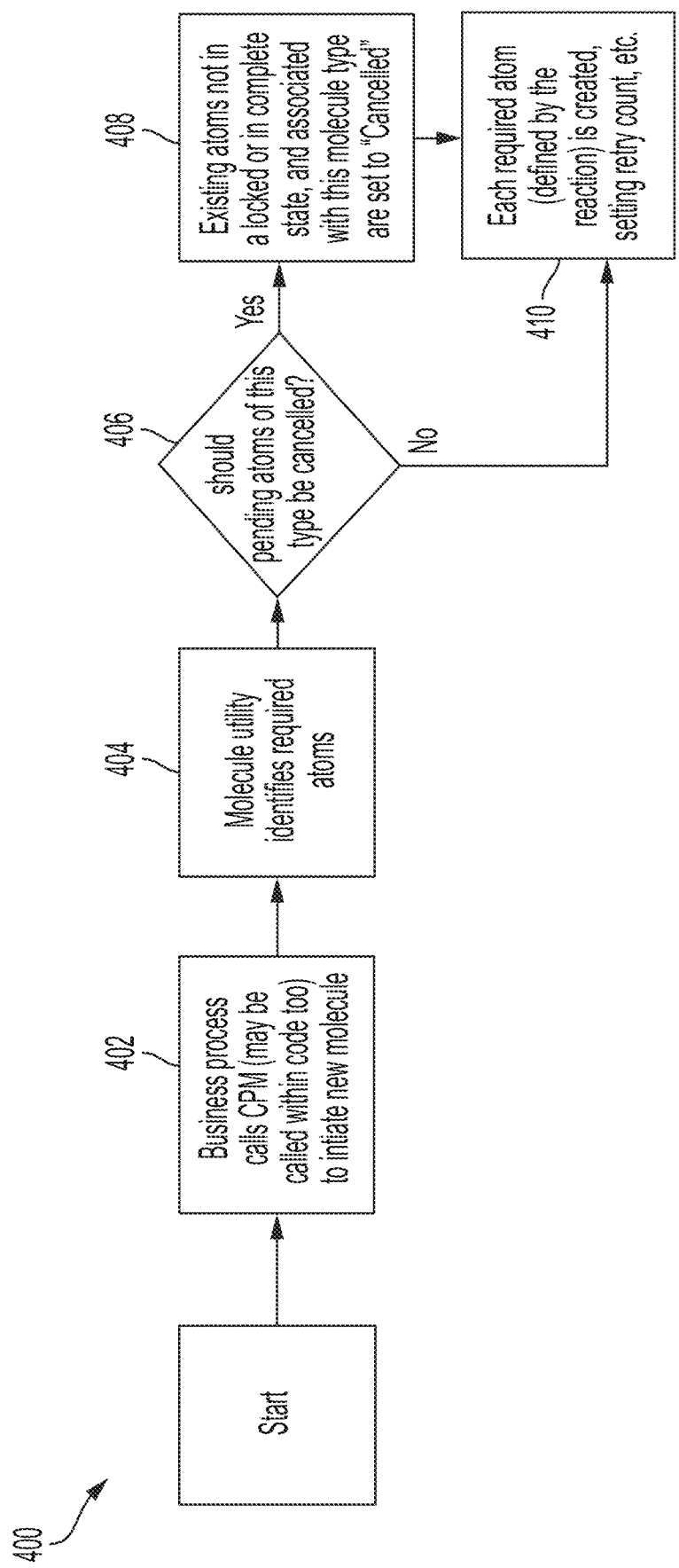
FIG. 4 illustrates an exemplary flow chart for a method of creating an instance of an exemplary routine in accordance with an embodiment of the present disclosure.

Referring to FIG. 4, there is illustrated an exemplary flow chart for a method of creating an instance of an exemplary routine in accordance with an embodiment of the present disclosure. The method 400 may include the step 402 of initiating a new instance of an exemplary routine. The initiation of a new instance of an exemplary routine may be caused by an existing business process CPM and/or a trigger within existing code operating within one or more servers of system 100 (e.g., a trigger set within a pre-programmed element running in an instance of an exemplary routine). Initiating an instance of an exemplary routine may include starting execution of code that creates a new instance of the exemplary routine. The step 402 may be initiated automatically (e.g., by a trigger) or by a user (e.g., an administrator 118, a developer 120). For example, a disposition on an incident being updated in database 110 and/or an inbound email having a specific subject being added to database 110.

The method 400 may include the step 404 of automatically identifying the pre-programmed elements that are included in the instance of the exemplary routine initiated in step 402. A processing LU operating in connection with processing server 102 may be configured to perform step 404. For example, the molecule utility function of the processing LU may identify the pre-programmed elements included in the instance of the exemplary routine. The method 400 may include the step 406 of determining whether the pre-programmed elements identified in step 404 should be cancelled. For example, in step 406 it may be determined whether the type of pre-programmed element and/or instance of the exemplary routine allows duplicates. An example of a pre-programmed element that allows duplicates may be an element that is configured to write a log file. An example of an instance of an exemplary routine that does not allow duplicates may be an instance of an exemplary routine that sends an electronic message to a customer. If the pre-programmed elements should be cancelled, the method 400 may progress to step 408 in which existing instances of pre-programmed elements not in a locked or complete state, that are included in the instance of the exemplary routine, are set to a cancelled state. If the pre-programmed elements should not be cancelled, the method 400 may progress to step 410 in which an instance of each required pre-programmed element, as defined by the instance of the exemplary routine, is created in database 110. The processing server 102 may be configured to perform steps 406-410 of method 400.

Figure 5:
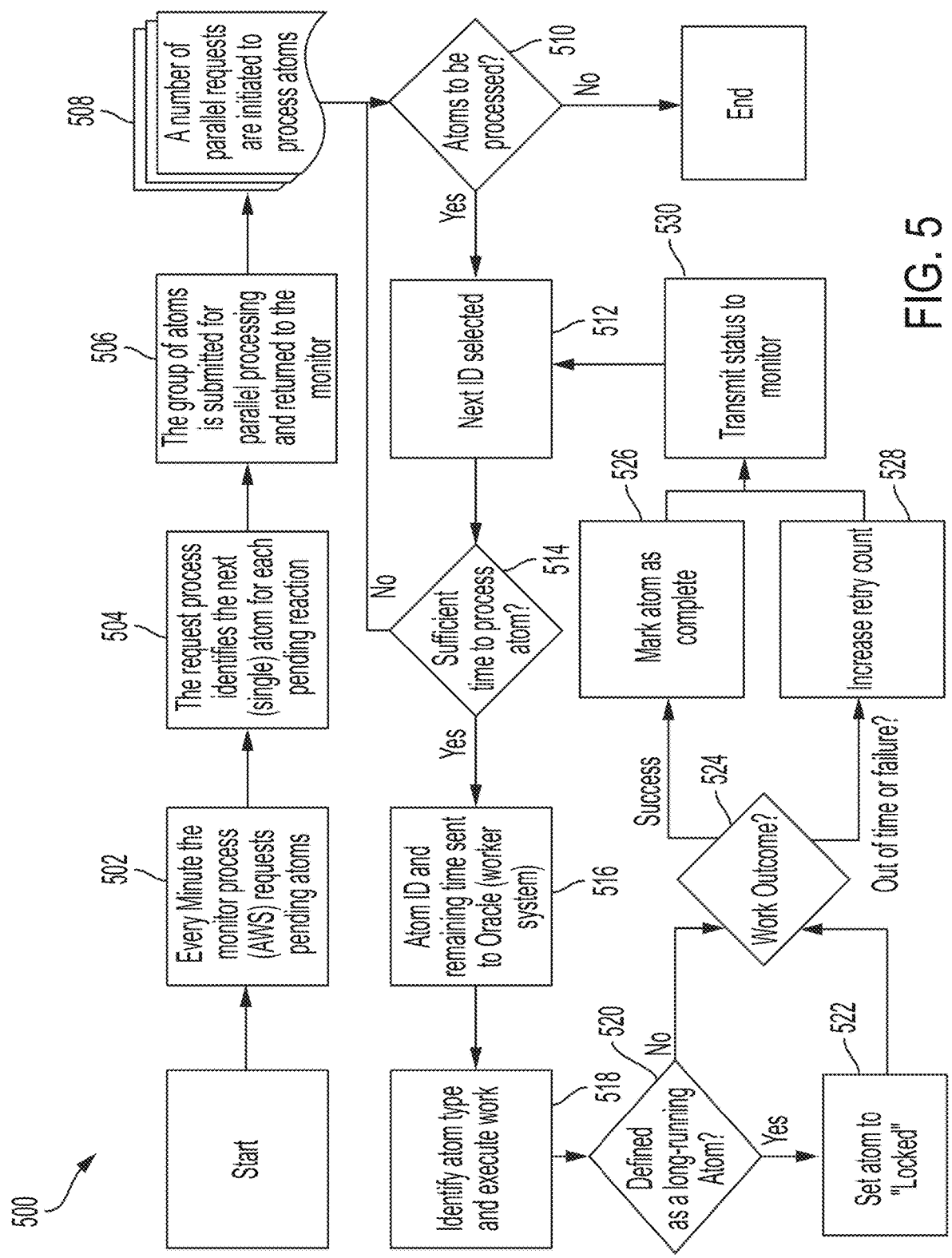
FIG. 5 illustrates an exemplary flow chart for a method of executing instances of pre-programmed elements in accordance with an embodiment of the present disclosure.

Referring to FIG. 5, there is illustrated an exemplary flow chart for a method of executing instances of pre-programmed elements in accordance with an embodiment of the present disclosure. The method 500 may include the step 502 of requesting pending pre-programmed elements at a predetermined interval (in FIG. 5 the predetermined interval is one minute). The pre-determined interval may be 30 seconds, 60 seconds, 90 seconds, 120 seconds, 150 seconds, or 180 seconds. The monitoring server 104 may be configured to perform step 502 (e.g., by access a monitoring LU). The method 500 may include the step 504 of identifying the next pre-programmed element for each instance of a pending exemplary routine. The processing server 102 may be configured to perform step 504. The method 500 may include the step 506 of submitting the pre-programmed elements identified in step 504 for parallel processing. The step 506 may further include returning the pre-programmed elements identified in step 504 to the monitoring server 104. For example, a list of IDs of the instances of pre-programmed elements that are pending are sent to monitoring server 104. In some embodiments, the IDs included in the list are specific to each instance of the pre-programmed elements. For example, there may be two unique IDs identifying different instances of the same pre-programmed element. The processing server 102 may be configured to perform step 506.

The method 500 may include the step 508 of initiating the parallel requests to process the pre-programmed elements. The method 500 may include the step 510 of determining whether there are pre-programmed elements to be processed. If there are pre-programmed elements to be processed, the method proceeds to step 512 in which the next ID corresponding to a pre-programmed element is selected. In step 512, the system 100 may be configured to divide the total number of pending instances of pre-programmed elements by the number of parallel requests, each request being assigned a set of IDs corresponding to instances of pre-programmed elements to iterate through. For example, pending instances of a pre-programmed element may be parsed into groups for parallel processing. The number of pending instances of pre-programmed elements that can be included in a single group of instances for parallel processing may be a configurable amount (e.g., 10, 20, 50, or 100 instances for each group for parallel processing). If there are no pre-programmed elements to be processed, execution may be terminated.

The method 500 may also proceed to step 514 following step 512 to determine if there is sufficient time to process an instance of the pending pre-programmed element. For example, the monitoring server 104 may determine, based on the frequency established in step 502 (e.g., one minute), if there is sufficient time remaining to process an instance of the pending pre-programmed element. The method 500 may include the step 516 of transmitting the pre-programmed element ID and the remaining time determined in step 514 to the worker server 106. The monitoring server 104 may be configured to perform steps 508 through 516. The method 500 may include the step 518 of identifying the pre-programmed element type and executing the code associated with the pre-programmed element type. The worker server 106 may be configured to perform step 518. The method 500 may include the step 520 of determining whether an executing pre-programmed element is defined as "long-running". A long-running pre-programmed element may be a pre-programmed element that takes an amount of time to finish execution that is greater than a predefined timeout value. For example, a predetermined timeout value may be five minutes and pre-programmed element A may take ten minutes to execute, resulting in pre-programmed element A being defined as long-running.

If the pre-programmed element is defined as long running, the method may proceed to step 522 to set the pre-programmed element as having a locked state. A locked state of an instance of a pre-programmed element may allow execution of that instance of the pre-programmed element to continue across multiple execution runs without execution of said instance being restarted. A single execution run may refer to the execution of instances of pre-programmed elements executing within the predetermined interval (e.g., one minute) defined in step 502. If the pre-programmed element is not defined as long-running, the method 500 may proceed to step 524 to determine the outcome of the executed pre-programmed element. If the pre-programmed element successfully executed, the method 500 may proceed to step 526 to mark the pre-programmed element as complete. If the pre-programmed element fails to execute or runs out of time, the method 500 may proceed to step 528 to increase the retry count associated with the instance of that pre-programmed element. The method 500 may include the step 530 of transmitting the status of an instance of the pre-programmed element to monitoring server 104. The method 500 may return to step 512, following the transmission of the status in step 530, such that the next ID corresponding to a pre-programmed element is selected and steps 514-530 are repeated for each pre-programmed element to be processed. The processing server 102 may be configured to perform steps 520 through 530.

Figure 6A:
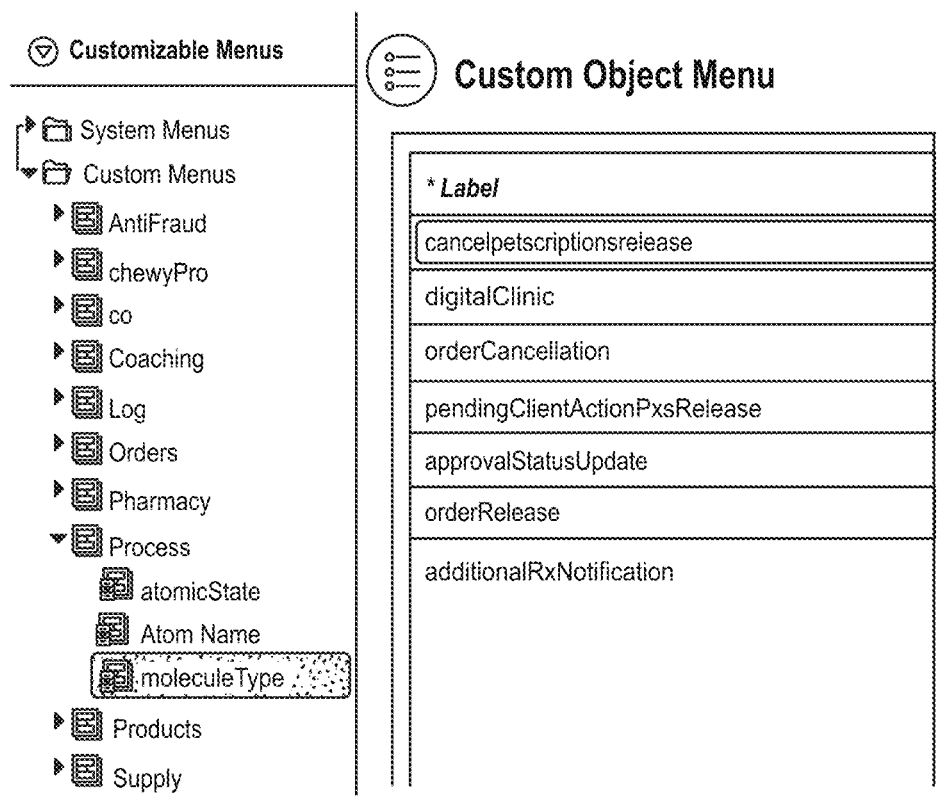
FIGS. 6A-6B illustrates an exemplary user interface for the creation of a new exemplary routine, in accordance with an exemplary embodiment of the present disclosure.
Figures 6B, 6C:
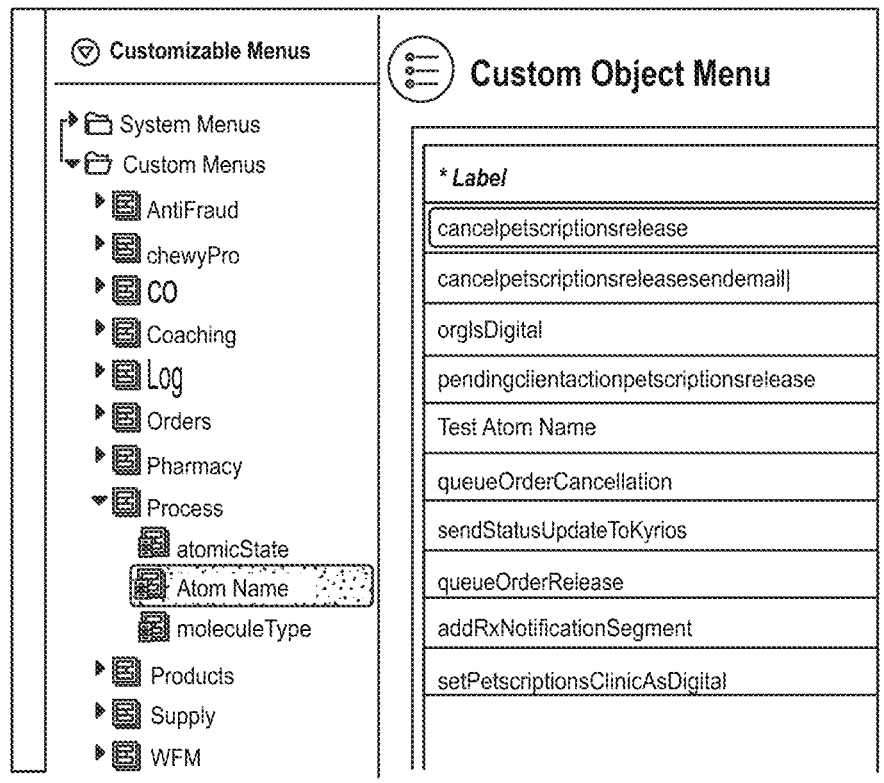
FIG. 6C illustrates an example of computer executable code associated with a pre-programmed element.

Referring to FIGS. 6A-6H, there is shown an exemplary user interface for the creation of a new exemplary routine and/or pre-programmed elements in accordance with an embodiment of the present invention. The exemplary user interfaces shown in FIGS. 6A-6H may be displayed on a client device 108 in communication with processing server 102. Processing server 102 may transmit the user-interfaces shown in FIGS. 6A-6H for display on client device 108 via a network (e.g., wireless network, ethernet network). The user interfaces illustrated in FIGS. 6A-6B and 6D-6H may be a portion of an administrator UI, as described above with reference to FIG. 1. Referring to FIG. 6A, an administrator 118, via client device 108, may define a new instance of an exemplary routine (e.g., may input a label for the new instance of the exemplary routine). Referring to FIG. 6B, the administrator 118, via client device, may provide input to create a new pre-programmed element type to be included in the instance of the exemplary routine shown in FIG. 6A. In this example, the administrator 118 creates a new pre-programmed element labeled "cancelpetscriptionreleasesendemail".

The administrator 118 may input a label that is representative of the task that the pre-programmed element is configured to accomplish. In this example the pre-programmed element is configured to notify a customer via an electronic message (e.g., email) that their prescription has been cancelled, which may occur after the prescription cancellation is successful. In one embodiment, the successful execution of an instance of an exemplary routine may be the trigger event for creation of a new instance of an exemplary routine.

For example, an instance of exemplary routine A successfully executes which triggers creations of an instance of exemplary routine B to be executed. Referring to FIG. 6C, the administrator 118, following the creation of the new pre-programmed element in FIG. 6B may coordinate with a developer 120 to develop the computer executable code for accomplishing the desired task. FIG. 6C displays an example of computer executable code, written by a developer 120, to accomplish the task of the pre-programmed element created in FIG. 6B. The computer executable code, written by the developer 120, may be self-contained and may be used across a plurality of different exemplary routines.

Figure 6D:
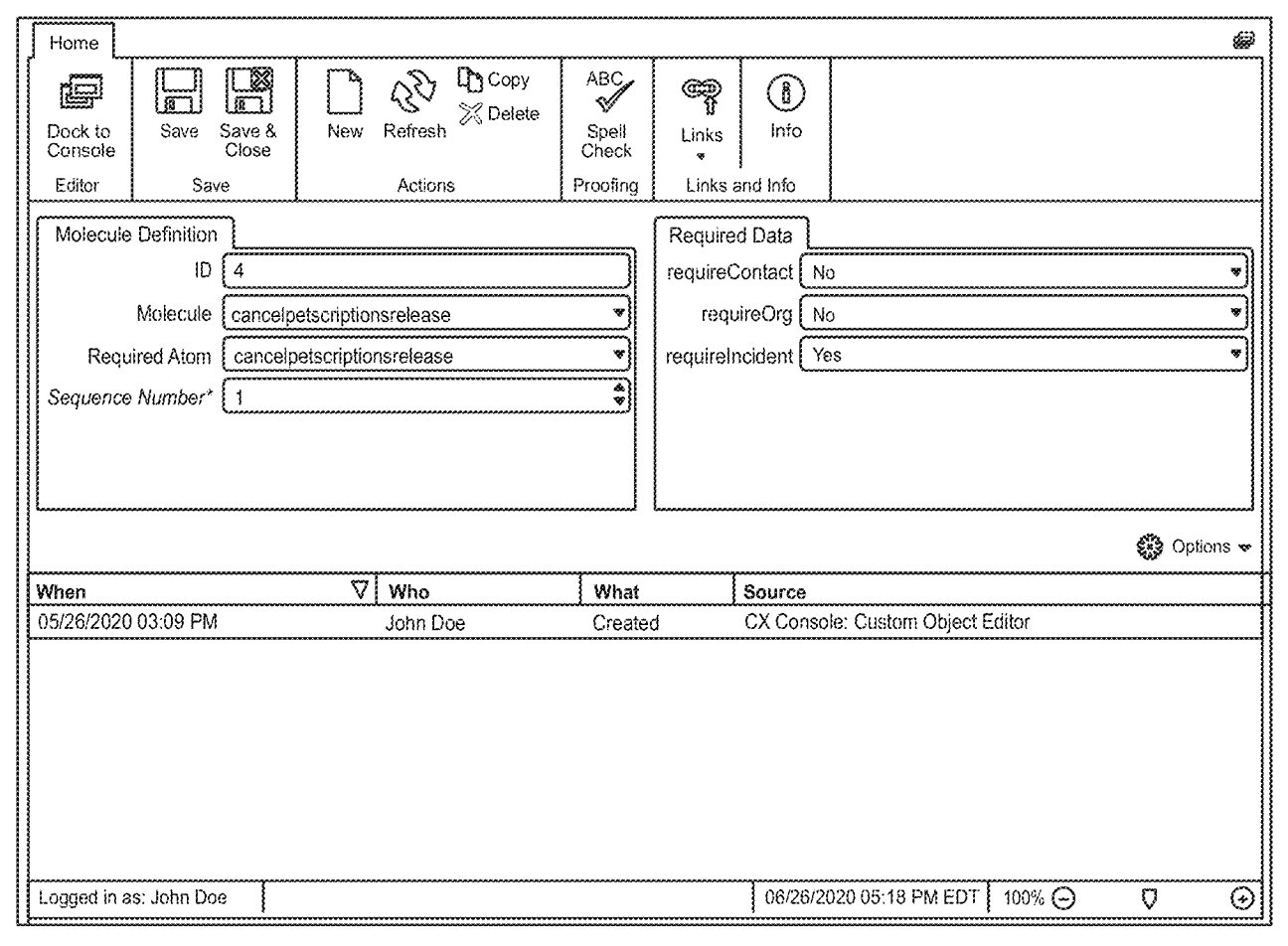
Figure 6E:
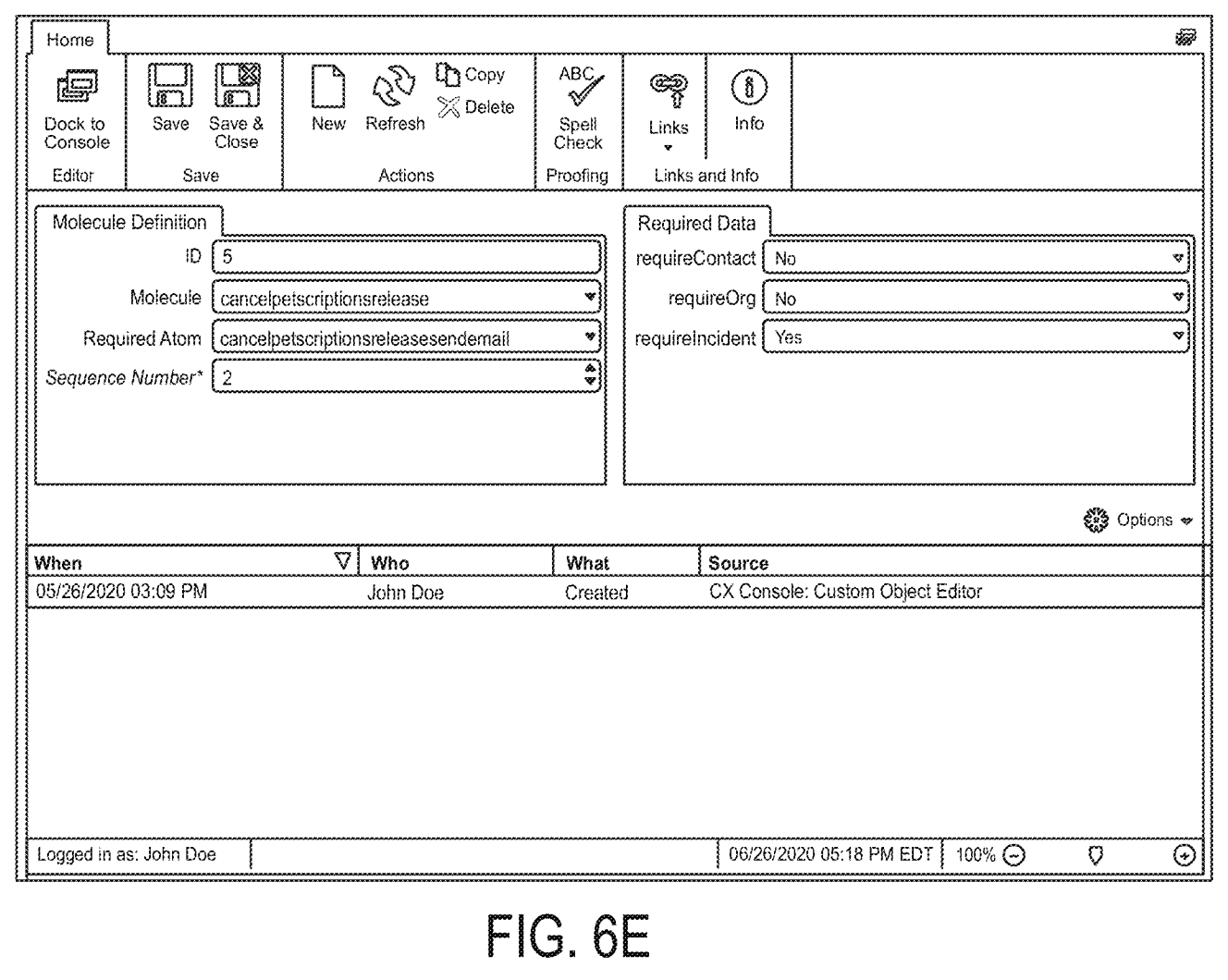

Referring to FIG. 6D, the administrator 118, via client device 108 may define an exemplary routine. The displayed administrator UI shown here may be configured to allow the administrator to input the exemplary routine, select a specific pre-programmed element included in the exemplary routine, and define the sequence number associated with said pre-programmed element. In the example shown here, the pre-programmed element "cancelpetscriptionrelease" is assigned a sequence number of "1" indicating that "cancelpetscriptionrelease" is to be the first pre-programmed element executed in this exemplary routine. Referring to FIG. 6E, the administrator 118, via client device 108, may add another pre-programmed element to the exemplary routine created in FIG. 6D. In this example, the administrator 118, adds the pre-programmed element "cancelpetscriptionreleasesendemail" to the exemplary routine and assigns a sequence number of "2" indicating that "cancelpetscriptionreleasesendemail" is to be the second pre-programmed element executed in this exemplary routine.

Figure 6F:
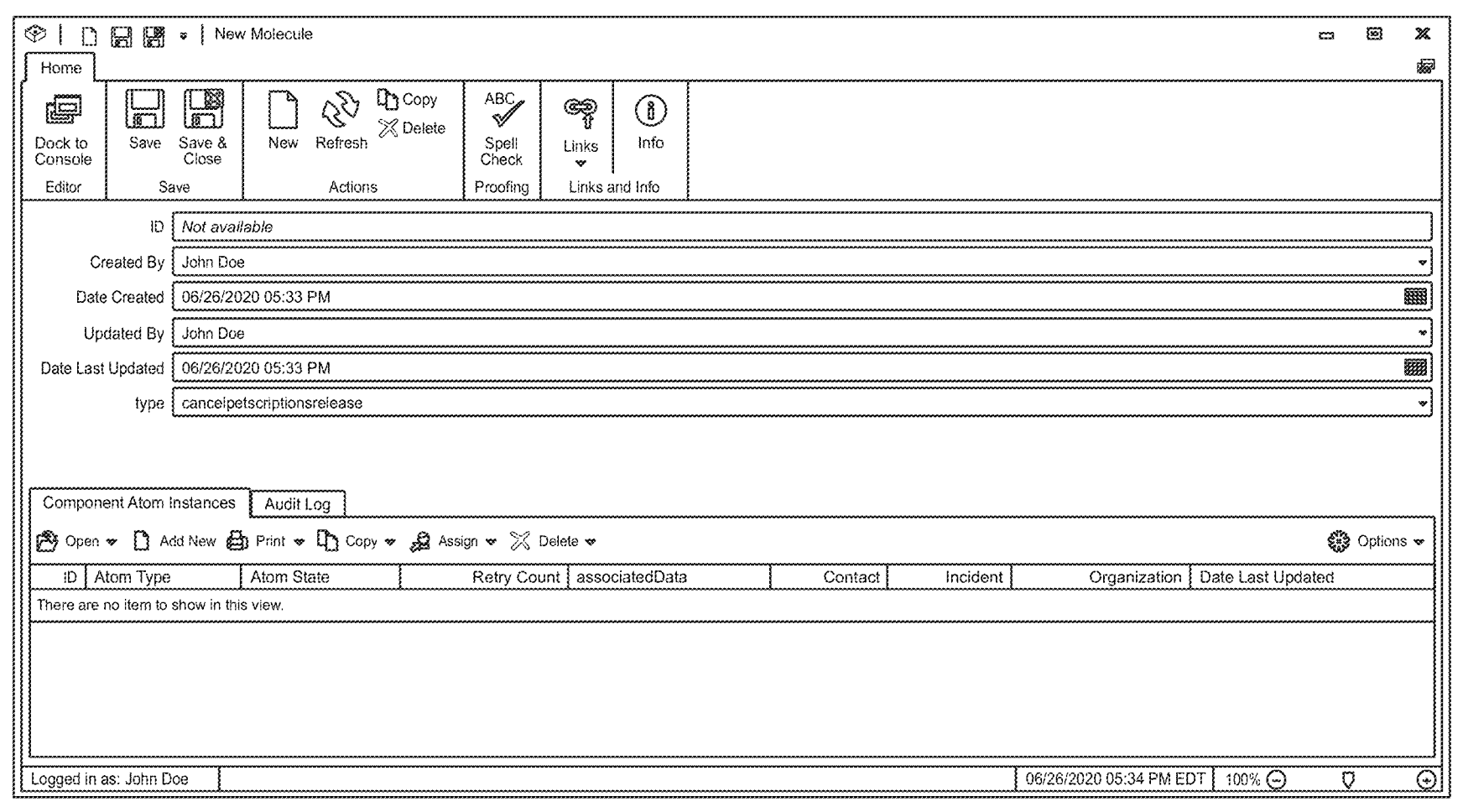
Figure 6G:
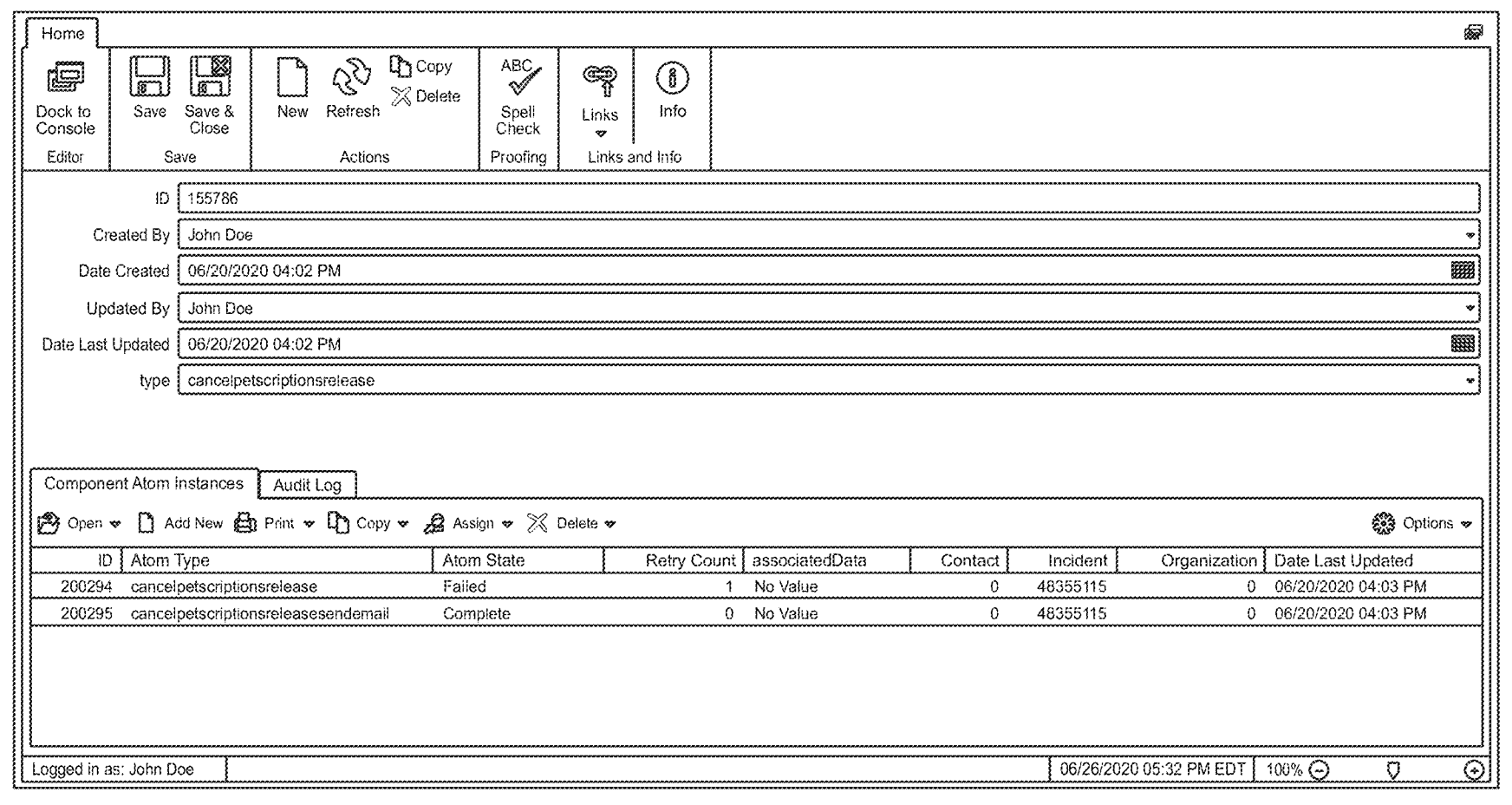

Referring to FIGS. 6F-6H, there is illustrated an exemplary user interface for creating and executing a new instance of an exemplary routine. Referring to FIG. 6F, an incident may trigger creation of an instance of an exemplary routine. In this example, the instance created is for the exemplary routine created by the administrator 118 in FIG. 6A.

The incident that triggers creation of the instance of an exemplary routine may be any one of: administrative workflow, custom code, or a new instance of a pre-programmed element (of a specific type) being created. Referring to FIG. 6G, upon creation of a new instance of an exemplary routine, the processing server 102 is configured to create instances of the pre-programmed elements included in the exemplary routine. The instances of the pre-programmed elements may be stored in database 110. In the example shown here, an instance report for the instances of pre-programmed elements is displayed. The displayed instance report may include information associated with each instance of pre-programmed elements including: an ID, the label, a state (e.g., the status), a retry count, associated data, contact data, an incident ID, an organization number, and the date last updated. Referring to FIG. 6H, the computer executable code for each instance of the pre-programmed elements is executed in sequence. A display of a completed instance of a pre-programmed element is displayed in FIG. 6H.

Figure 6I:
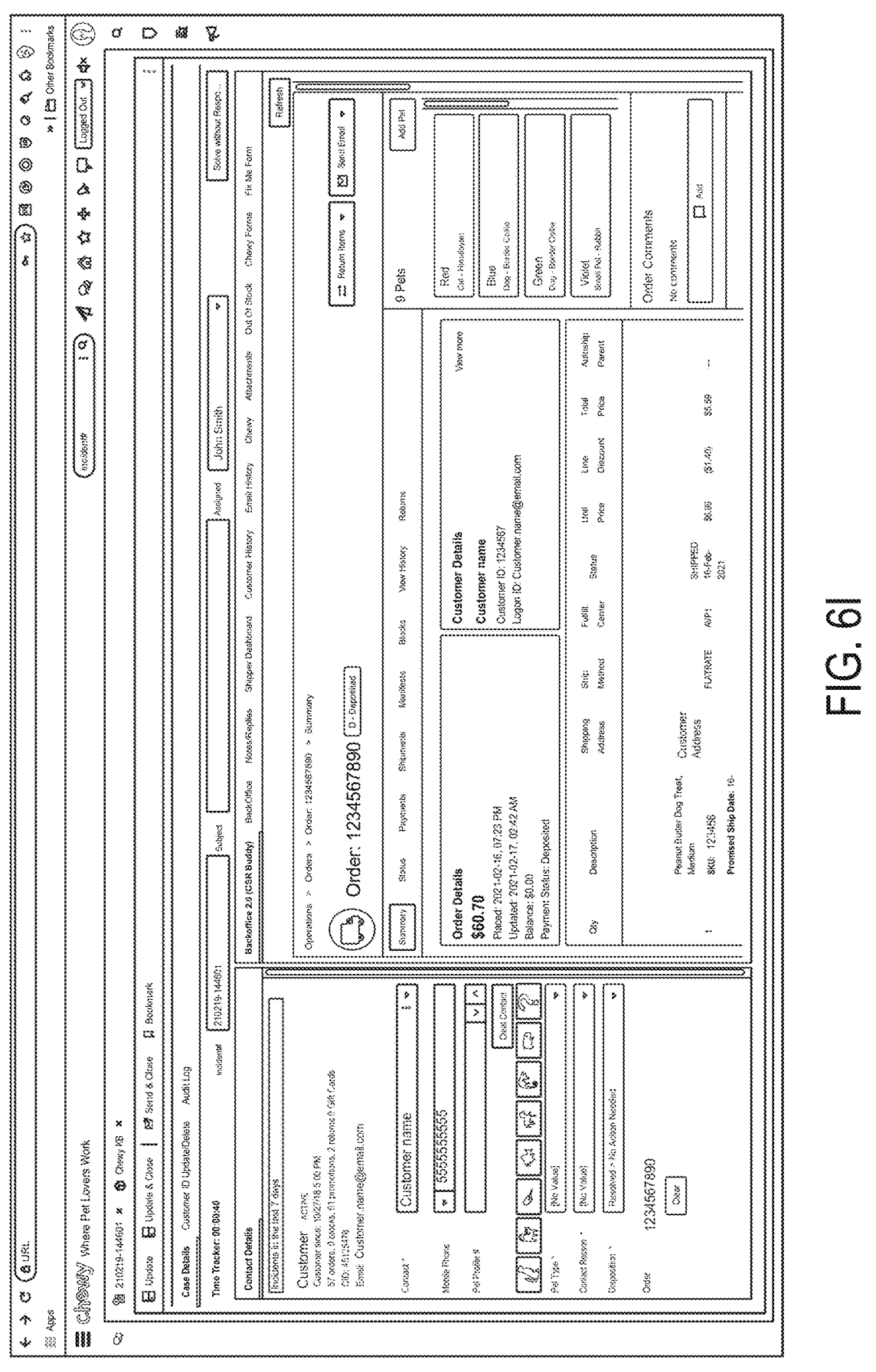

Referring to FIG. 6I there is shown a customer service user interface displayed on a client device 108 in accordance with an exemplary embodiment of the present invention. The processing server 102 may be configured to transmit the customer service user interface for display on the client device 108. The customer service user interface may include information specific to a customer and/or an order placed, via storefront server 107, by said customer. In the customer service UI example displayed in FIG. 6I, information relating to the customer and an order placed by the customer is shown. The customer service UI may display user-operable buttons configured to allow an admin 118 to take actions related to the displayed order and/or customer. For example, the customer service UI may display buttons that allow an admin 118 to request a return of the ordered product, email the customer, associate a pet with the customer, and/or edit customer contact information. The processing server 102 may be configured to, in response to an input from an admin 118 on the customer service UI, trigger creation of an instance of an exemplary routine corresponding to the input from the admin 118. For example, an admin 118 may input on customer service UI to request a return for a product ordered by the customer. In response to the input from admin 118, the processing server 102 may execute code to create an instance of an exemplary routine configured to process a request to return said product and store said instance of the exemplary routine in database 110 for execution.

Figure 7:
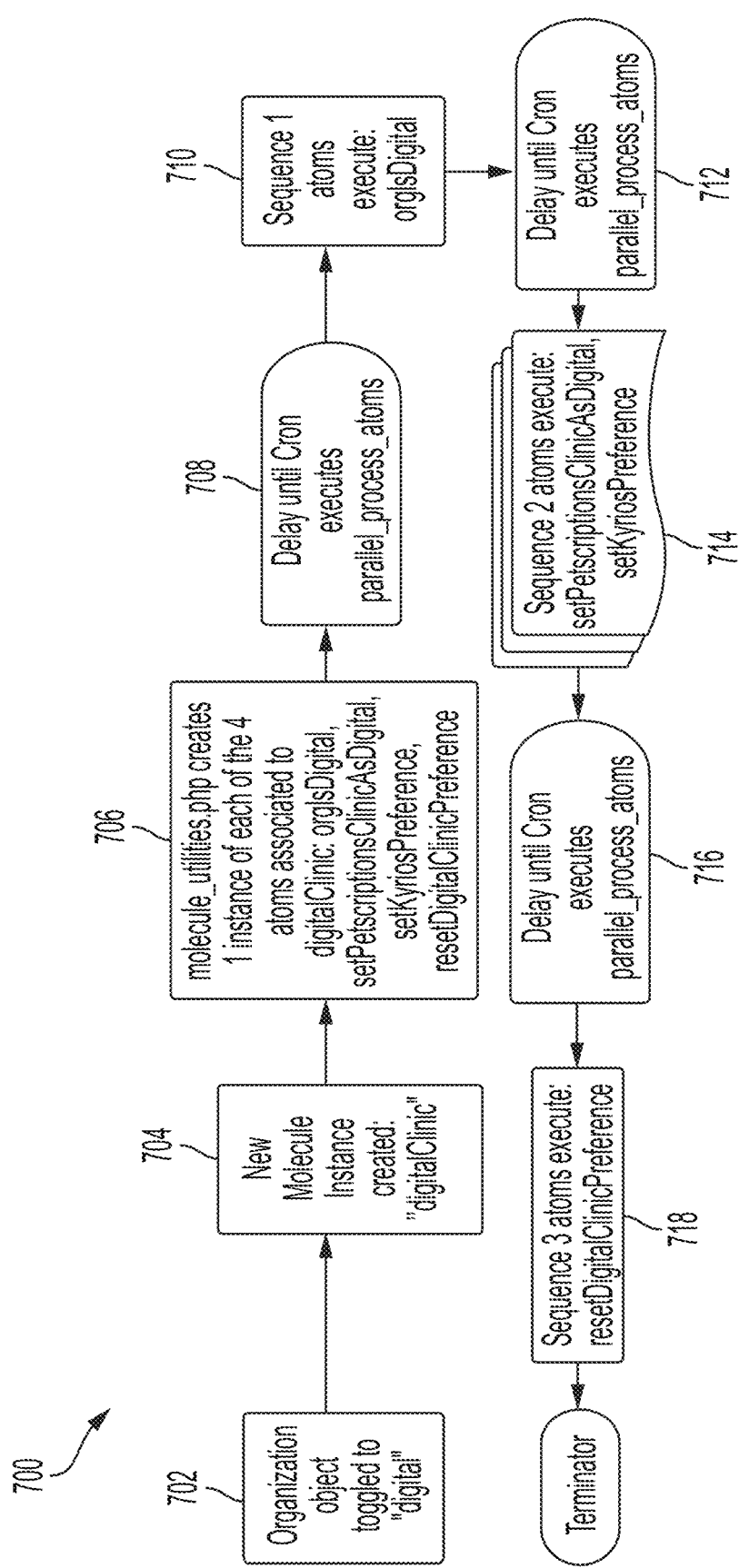
FIG. 7 illustrates an exemplary flowchart for a method of execution of an instance of an exemplary routine, in accordance with an exemplary embodiment of the present disclosure.

Referring to FIG. 7, there is illustrated an exemplary flowchart for a method of execution of an instance of an exemplary routine. The method 700 shown in FIG. 7 represents an exemplary method implemented by system 100 without any interruptions (e.g., failure to execute pre-programmed elements, changes in underlying data). The method 700 may start at step 702 in response to a trigger event (e.g., an incident). The trigger event may be an organization object being toggled to "digital". An organization object being toggled to "digital" may refer to an indication in database 110 that a veterinary clinic should use a prescription authorization service offered by a host of the processing server 102 (e.g., Petscriptions by Chewy) or a fax to authorize prescriptions. The method 700 may include step 704 where an instance of an exemplary routine is created. The method 700 may include the step 706 where instances of pre-programmed elements included in the instance of the exemplary routine are created. The method 700 may include the step 708 where processing is delayed until Cron executes, which may refer to a time-based scheduler that defines a configurable set of time between execution of different instances of pre-programmed elements. The method 700 may include the step 710 where an instance of a pre-programmed element that is listed as the first pre-programmed element in a sequence defined by the instance of the exemplary routine is executed. The method 700 may include the step 712 where processing is delayed. The method 700 may include the step 714 where one or more instances of pre-programmed elements are executed in parallel. In some embodiments, step 710 may also include parallel execution of instances of pre-programmed elements. In some embodiments, step 714 executes only one instance of a pre-programmed element. The instances of pre-programmed elements executed in step 714 may correspond to the next sequence of pre-programmed elements as defined by one or more instances of exemplary routines. The method 700 may include step 716 where processing is delayed. The method 700 may include step 718 where an instance of a pre-programmed element next in the sequence is executed. It will be understood that the method 700 is an example, and that in practice any number of instances of pre-programmed elements may be executed according to a corresponding sequence defined by an instance of an exemplary routine.

In some embodiments, instances of exemplary routines that have successfully executed and/or failed to execute are stored as records in database 110 for auditing purposes. An instance of an exemplary routine, once it has successfully executed or failed to successfully execute, may have the status indicator updated respectively. For example, an instance of an exemplary routine may include a "success" indicator for each instance of pre-programmed elements included in the instance of the exemplary routine that successfully executed and a "failed" status indicator for instances of pre-programmed elements that failed to execute.

Figure 8:
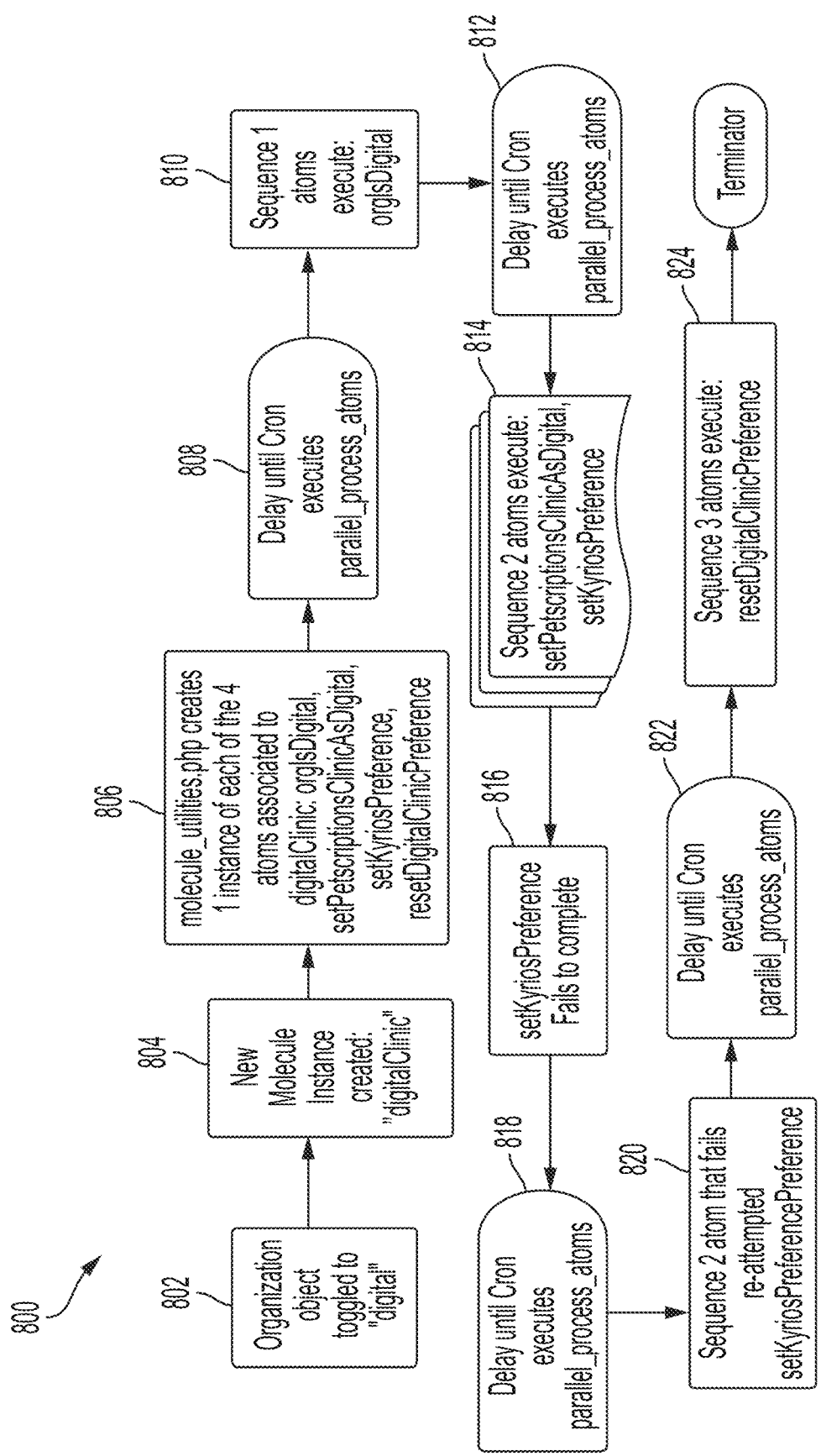
FIG. 8 illustrates an exemplary flowchart for a method of execution of an instance of an instance of an exemplary routine where a pre-programmed element fails to execute, in accordance with an exemplary embodiment of the present disclosure.

Referring to FIG. 8, there is illustrated an exemplary flowchart for a method of execution of an instance of an exemplary routine where a pre-programmed element fails to execute. The method 800 may be similar to the method 700, shown in FIG. 7, except that an instance of a pre-programmed element fails to execute. Specifically, the steps 802 to 814 of method 800 correspond to the steps 702 to 714 of method 700 and will not be repeated for sake of brevity. In the method 800, execution of the second sequence of an instance of a pre-programmed element fails. Following the instance of the pre-programmed element failing to execute, the method 800 includes the step 816 of setting the pre-programmed element to a failed status. The method 800 may include a delay in processing at step 818. The method 800 may include the step 820 of attempting execution of the previously failed pre-programmed element one more time. In the method 800, the attempt at executing the instance of the pre-programmed element in step 820 is successful and the instance of the pre-programmed element executes. Following the successful execution of the instance of the pre-programmed element, method 800 proceeds to steps 822 to 824, which correspond to steps 716 and 718 of method 700 and will not be described again for sake of brevity.

Figure 9:
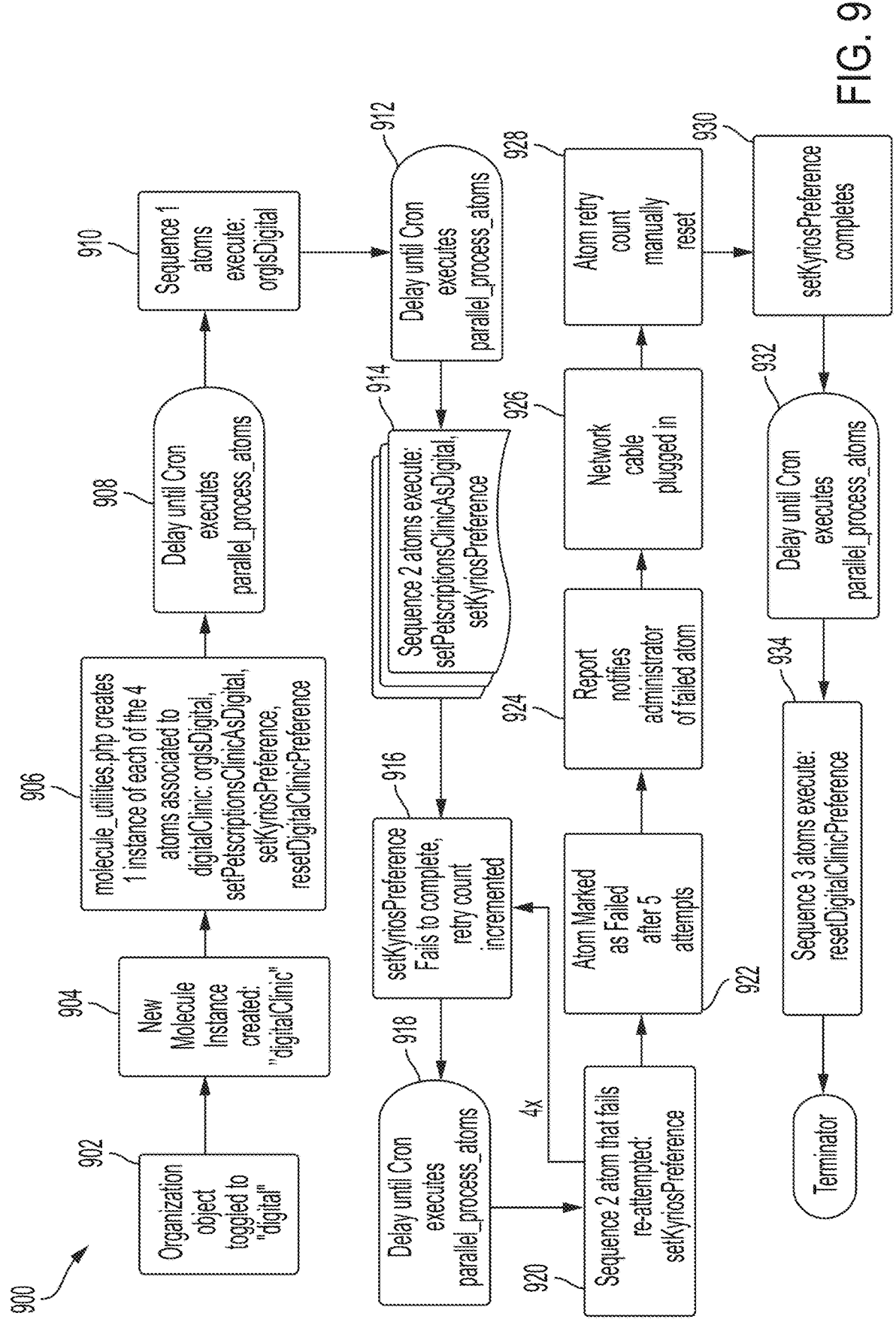
FIG. 9 illustrates an exemplary flowchart for a method of execution of an instance of an instance of an exemplary routine where a pre-programmed element permanently fails to execute, in accordance with an exemplary embodiment of the present disclosure.

Referring to FIG. 9, there is illustrated an exemplary flowchart for a method of execution of an instance of an exemplary routine where a pre-programmed element permanently fails to execute. The method 900 is similar to the method 800 except that the instance of the pre-programmed element that fails to execute does not successfully execute after a certain number of attempts. Specifically, the steps 802 to 818 of method 800 correspond to the steps 902 to 918 of method 900 and will not be repeated for sake of brevity. In this example, after the first reattempt fails, the method 900 returns to step 916 and increments a retry count associated with the instance of the pre-programmed element by 1. The method 900 then attempts, a certain number of times, to successfully execute the instance of the pre-programmed element. In this example, the total number of attempted retries is five (a first reattempt followed by four more). The instance of the pre-programmed element fails to execute in each attempt and a retry threshold is reached. The retry threshold may be a predetermined amount established by a user (e.g., administrator 118, developer 120).

Following the reattempts to execute the instance of the pre-programmed element, the method 900 may include step 922 in which the instance of the pre-programmed element is marked as failed. The step 922 may also include adding the instance of the pre-programmed element to a list of instances of pre-programmed elements that failed to execute after a certain number of retries. The method 900 may include the step 924 of automatically generating and sending a report that notifies administrators 118 and/or developers 120 of all instances of pre-programmed elements that failed to execute after a certain number of retries. The system 100 may be configured to automatically perform step 924 at a predetermined interval (e.g., every 6 hours, every 12 hours, every 24 hours, every 3 days, every week). The method 900 may include the step 926 of resolving the error causing the failure of the instance of the pre-programmed element. For example, the error may be caused by a network cable not being plugged in, which requires an administrator to manually connect a network cable. In other embodiments the system 100 may be configured to automatically resolve the error. The method 900 may include the step 928 of manually resetting the retry count for the instances of the failed pre-programmed elements. Step 928 may be performed after the error has been resolved. In some embodiments, resetting the retry count for the failed instances of pre-programmed elements may cause execution to be reattempted for said instances. The method 900 may include the step 930 of setting the instance of the failed pre-programmed element to complete. Step 930 may be performed after an admin 118 or developer 120 has manually fixed the error which caused the instance of the pre-programed element from step 920 to fail. Following step 930, method 900 proceeds to steps 932 to 934 which correspond to steps 822 and 824 of method 800 and will not be described again for sake of brevity.

Figure 10:
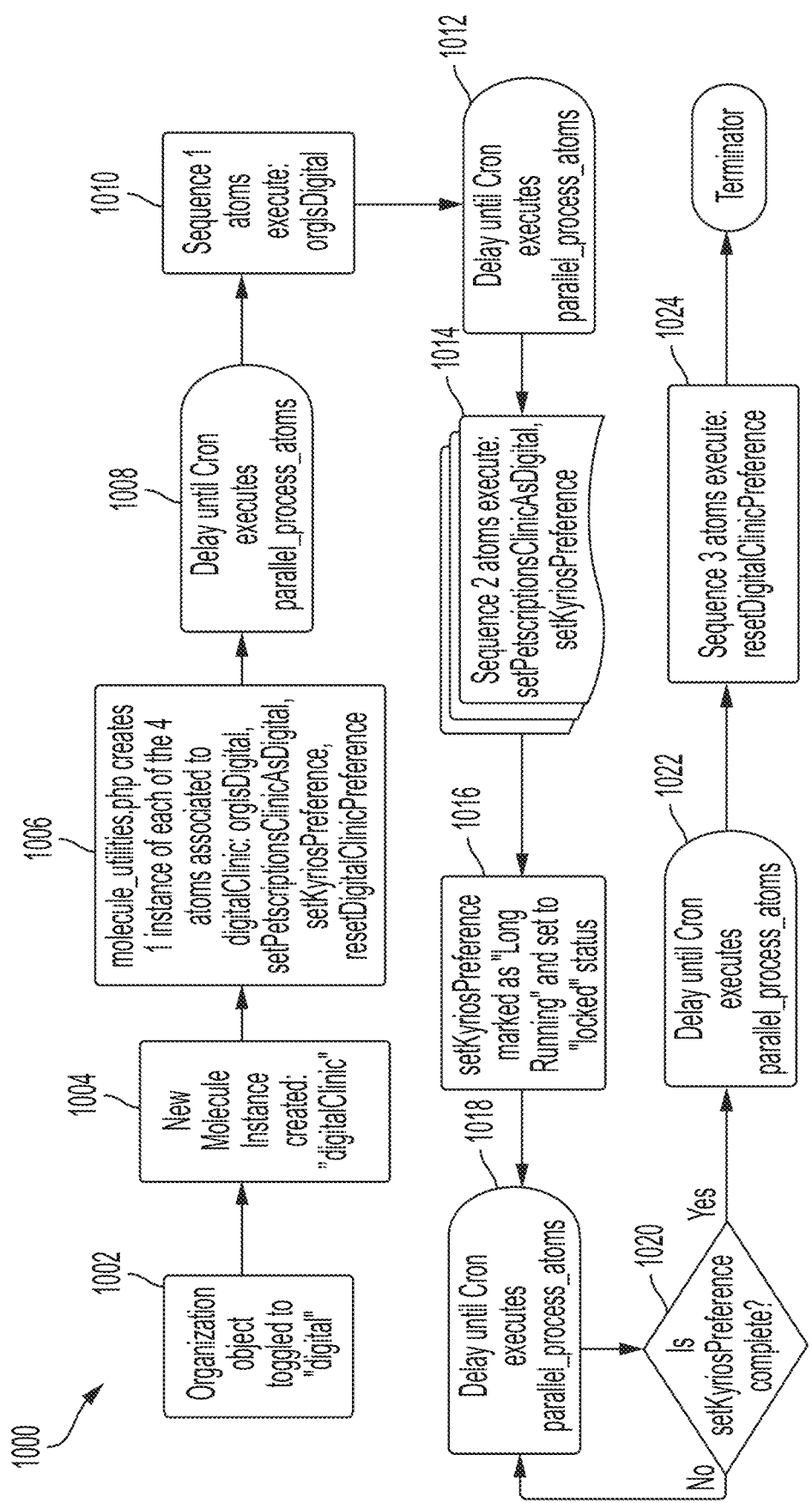
FIG. 10 illustrates an exemplary flowchart for a method of execution of an instance of an exemplary routine with a long-running pre-programmed element, in accordance with an exemplary embodiment of the present disclosure.

Referring to FIG. 10, there is illustrated an exemplary flowchart for a method of execution of an exemplary routine with a long-running pre-programmed element. The method 1000 may be similar to the method 700 shown in FIG. 7, except that there is an instance of a long-running pre-programmed element to be executed. Specifically, the steps 1002 to 1014 of method 1000 correspond to the steps 702 to 714 of method 700 and will not be repeated for sake of brevity. In the method 1000, there is an instance of a long-running pre-programmed element that begins executing at step 1014. The method 1000 includes the step 1016 of marking the instance of the long-running pre-programmed element as "long-running" and setting it to a "locked" status. The method 1000 includes the step 1018 of delaying processing. The method 1000 includes the step of determining whether the instance of the long-running pre-programmed element is complete. If the instance long-running pre-programmed element has not finished executing, the method 1000 repeats step 1018 (e.g., continues to delay processing). If the instance of the long-running pre-programmed element has finished executing, the method 1000 continues to steps 1022 and 1024 which correspond to steps 716 and 718 of method 700 and will not be described again for sake of brevity.

Figure 11:
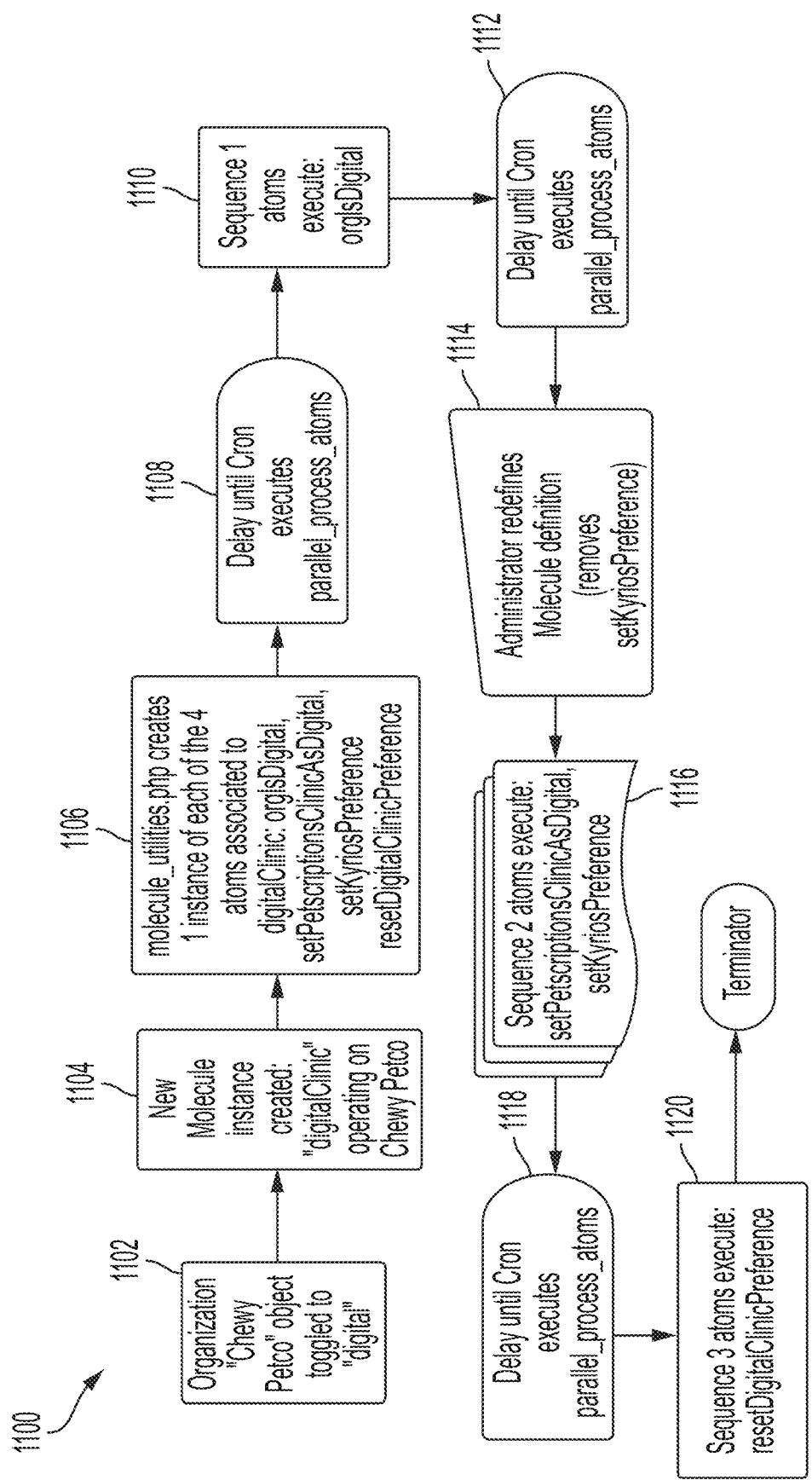
FIG. 11 illustrates an exemplary flowchart for a method of execution of an instance of an exemplary routine where the exemplary routine is updated mid-execution, in accordance with an exemplary embodiment of the present disclosure.

Referring to FIG. 11, there is illustrated an exemplary flowchart for a method of execution of an instance of an exemplary routine where the exemplary routine is updated mid-execution. The method 1100 may be similar to the method 700 shown in FIG. 7, except that there is the exemplary routine is redefined while an instance of the exemplary routine is being executed. Specifically, the steps 1102 to 1112 correspond to the steps 702 to 712 of method 700 and will not be repeated for the sake of brevity. In the method 1100, following the delay in processing at step 1112, an administrator 118, at step 1114, redefines the exemplary routine that the instance currently being executed corresponds to. In this example, an administrator 118 removes a pre-programmed element from the exemplary routine. It will be understood that a modification to the exemplary routine may include any modification that would cause an instance of an exemplary routine, created subsequent to the instance currently executing and the modification being performed, to execute differently than a previously executed and/or currently executing instance of said exemplary routine. For example, a modification may include a modification to the sequence defined by the exemplary routine, the addition of a pre-programmed element to the exemplary routine, and/or the removal of a pre-programmed element from the exemplary routine.

The method 1100 proceeds, at step 1116, to execute the instances of pre-programmed elements that were included in the instance of the exemplary routine prior to the administrator 118 removing the pre-programmed element at step 1114. Following step 1114, the method 1100 proceeds to steps 1116 through 1120 that correspond to steps 714 to 718 of method 700 and will not be described again for sake of brevity. In this example, the grouping was redefined while an instance of it was executing, and therefore the instance may be executed based on the grouping prior to the change made by the administrator 118 at step 1114. However, future instances of the same grouping may execute according to the change made by the administrator 118 in step 1114. It will be understood that the redefining of the exemplary routine instances may happen at any point after step 1104 and prior to termination of the instance of the pre-programmed element without affecting the outcome of the instance of the pre-programmed element.

In some embodiments, some instances of exemplary routines are the same (e.g., contain the same or substantially the same code and point to the same data or types of data). In some embodiments, some of the plurality of instances of exemplary routines differ from one another (e.g., the code may have been changed or the data may have changed in an intervening time period between the creation of instances of exemplary routines). For example, the code associated with a particular pre-programmed element may be changed after a first instance of an exemplary routine is created. That first instance would persist in that the original pre-programmed element code would remain unchanged, but future instances of such exemplary routine would reflect the new code. For example, in some instances there may be instances of exemplary routine X stored in database 110 and instances of different exemplary routines Y stored in database 110. For example, a first instance of exemplary routine X may be configured to cancel an order for customer A (e.g., the first instance was created in response to an incident to cancel an order from customer A) and a second instance of exemplary routine X may be configured to cancel an order for customer B (e.g., the second instance was created in response to an incident to cancel an order from customer B). Both the first and second instance of exemplary routine X may be stored in database 110. At a later point in time there may be a modification to exemplary routine X, and subsequent to that point in time there may be an instance of exemplary routine X created to cancel an order for customer C. In one embodiment, the configuration of the instances of the exemplary routine for customer A and customer B would be the same and would differ from the instance of the exemplary routine for customer C.

Figure 12:
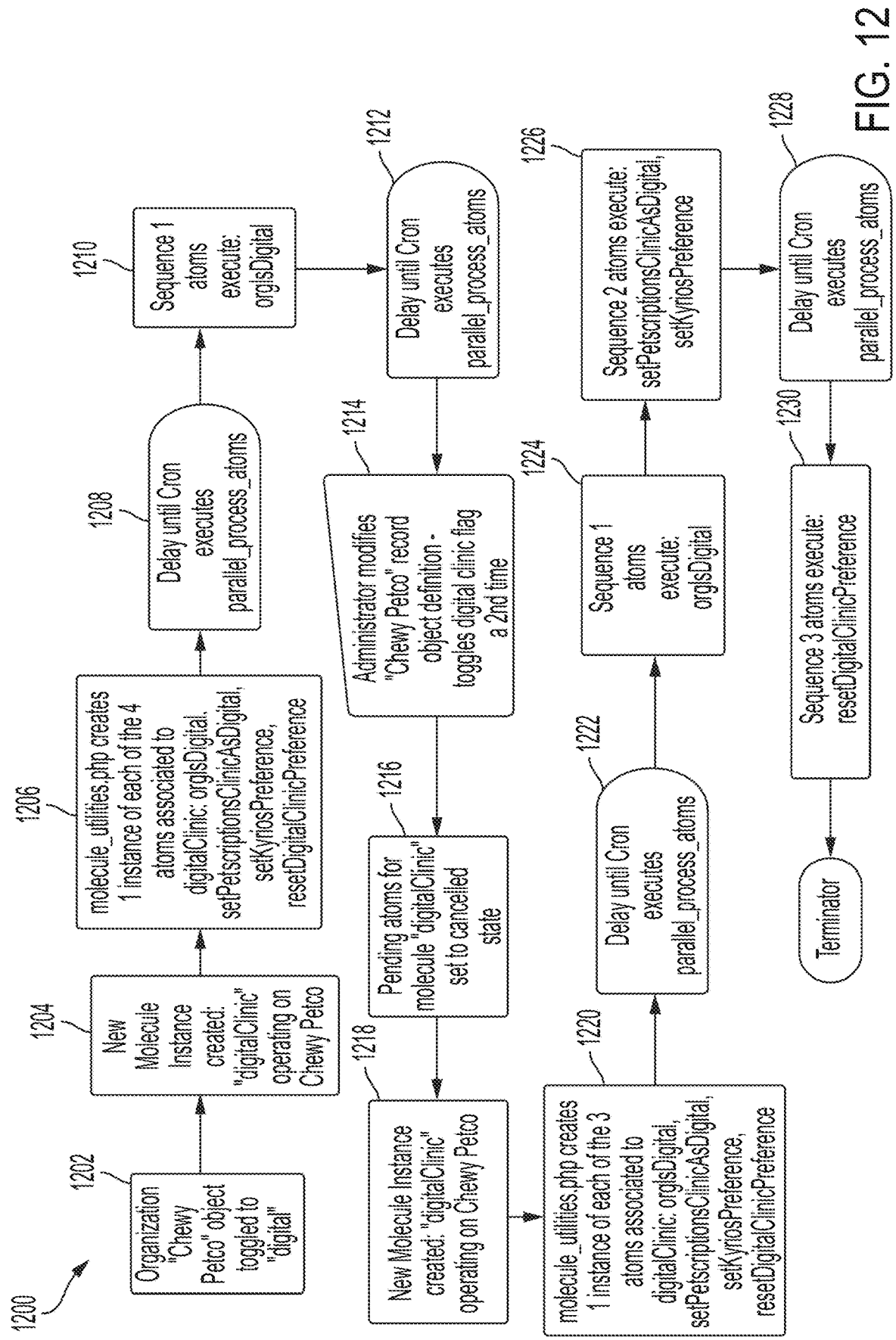
FIG. 12 illustrates an exemplary flowchart for a method of execution of an instance of an exemplary routine where underlying records are modified mid-execution, in accordance with an embodiment of the present disclosure.

Referring to FIG. 12, there is illustrated an exemplary flowchart for a method of execution of an instance of an exemplary routine where underlying records are modified mid-execution. The method 1200 may be similar to the method 700 shown in FIG. 7, except that underlying records required for the instances of the pre-programmed elements to execute are modified mid-execution. Specifically, the steps 1202 to 1212 correspond to steps 702 to 712 of method 700. Following the delay in processing 1212, an administrator modifies a record required by one or more of the instances of pre-programmed elements created in step 1206. The method 1200 continues to step 1216 to cancel the instance of the exemplary routine. The method continues to step 1218 to create a new instance of the exemplary routine which may correspond to the same exemplary routine for which the instance cancelled in step 1216 was originally created. To put it another way, in steps 1216 and 1218, the currently executing instance of the exemplary routine is cancelled and restarted. Following the restart at step 1218, the method 1200 continues to steps 1220 through 1230, which correspond to steps 706 to 718 of method 700 and will not be described again for sake of brevity.

Figure 13:
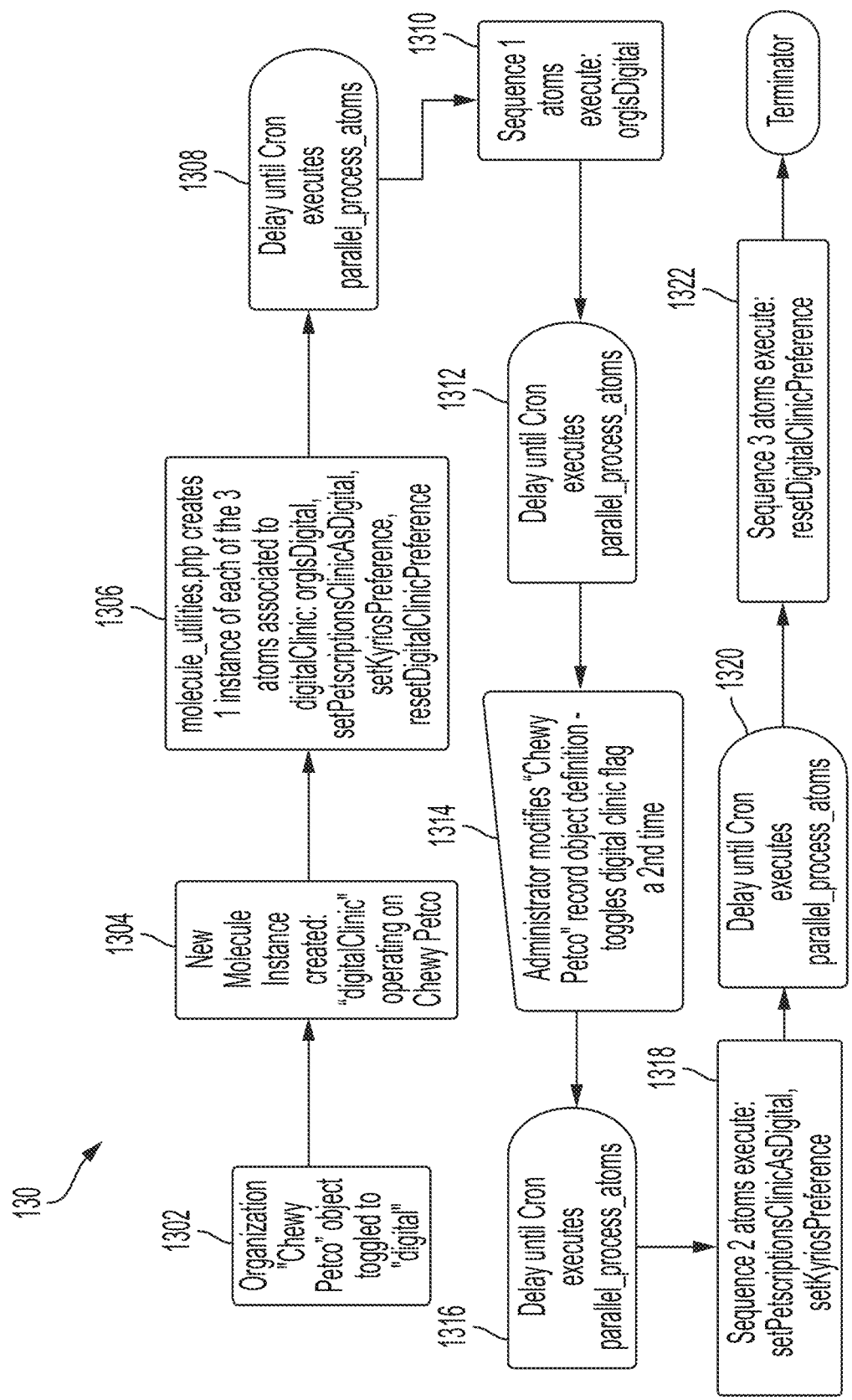
FIG. 13 illustrates an exemplary flowchart for a method of execution of an instance of an exemplary routine when underlying records are modified mid-execution, in accordance with another embodiment of the present disclosure.

Referring to FIG. 13, there is illustrated an exemplary flowchart for a method of execution of an instance of an exemplary routine where underlying records are modified mid-execution. The method 1300 may be similar to the method 1200, except that the instance of the exemplary routine that is currently executing is not cancelled and restarted. Steps 1302 to 1314 correspond to steps 1202 to 1214 of method 1200. However, in method 1300, following the modification of records, the instance of the exemplary routine created at step 1304 continues to execute through steps 1316 to 1322. Put another way, regardless of the modification of the underlying records, the currently executing instance is not cancelled and restarted. Steps 1316 to 1322 correspond to steps 712 to 718 of method 700 shown in FIG. 7, and will not be described again for sake of brevity.

Referring to FIG. 14, there is shown a flow diagram of an exemplary method 1400 for performing a fault tolerant automated sequence of computer implemented tasks. In an embodiment, the method 1400 includes a step 1402 of presenting, for selection by a user (e.g., administrator 118), a plurality of pre-programmed elements, each pre-programmed element being independently executable relative each other pre-programmed element such that an output of any of the pre-programmed elements is not a direct input to any other of the pre-programmed elements. For example, an administrator 118 via a client device 108 in communication with processing server 102 displays the admin UI to allow the administrator to create an instance of an exemplary routine as shown in FIGS. 6A-6B. In an embodiment, method 1400 also includes the step 1404 of receiving from the user a selection of one or more of the pre-programmed elements and a sequence for performing each pre-programmed elements in the selection to form an exemplary routine. For example, an administrator 118, via client device 108, creates an exemplary routine as shown in FIGS. 6E-6F.

In some embodiments, the method 1400 also includes the step 1406 of creating an instance of the exemplary routine in response to a request to implement the exemplary routine. A request to implement an exemplary routine may be a request to perform a series of tasks in response to an incident, as described above. In some embodiments, the instance of the exemplary routine includes an instance of each of the selected pre-programmed elements arranged for performance in accordance with the sequence and is configured to perform tasks defined by the pre-programmed elements and the sequence. For example, at steps 702 to 706 of method 700, an instance of an exemplary routine is created in response to a trigger event and instances of each pre-programmed element included in the exemplary routine are created. In an embodiment, the method 1400 also includes the step 1408 of initiating implementation of the instance of the exemplary routine by initiating performance of the instances of the pre-programmed elements in accordance with the sequence. For example, at steps 710 to 718 of method 700, the instances of the three pre-programmed elements included in the exemplary routine are executed in sequence. In an embodiment, the method 1400 also includes the step 1410 of detecting an error that prevents the completion of at least one instance of the pre-programmed elements. For example, in step 816 of method 800, an instance of the second pre-programmed element in the sequence defined by an instance of an exemplary routine is detected. In an embodiment, the method 1400 also includes the step 1412 of terminating the implementation of the instance of the exemplary routine upon detection of the error without user intervention. For example, in steps 916 to 922 of method 900 an instance of a pre-programmed element fails after a certain number of retries and the instance of the exemplary routine is automatically terminated.

In some embodiments, the independently executable pre-programmed elements of method 1400 may not require data generated from another pre-programmed element in order to complete execution. In some embodiments, each independently executable pre-programmed element completes using data from a data field, where the data is at least one of: i) populated in the data field before the creating of the instance of the exemplary routine; and ii) updated after the initiating of the implementation of the instance. For example, each instance of a pre-programmed element may use data stored in database 110 that was stored prior to the creation of the instance of the pre-programmed element or data that was updated in database 110 after the instance of the pre-programmed element was created.

In some embodiments, the method 1400 may include transmitting a notification that at least one instance of a pre-programmed element did not execute to completion and the notification includes at least one of: i) all instance of exemplary routines that are in a failed state at the time the notification is transmitted; ii) the instances of a pre-programmed elements associated with each instance of exemplary routines that are in the failed state; iii) the instance of the exemplary routine; iv) a number of retries associated with each instance of the exemplary routine in the failed state; and v) a database object associated with each instance of the exemplary routine in the failed state. For example, in step 924 of method 900 a report is sent to administrators 118 including a listing of all instances of pre-programmed elements that failed to execute. Administrators 118 may then review and/or analyze the instance of the pre-programmed element and/or the associated exemplary routine on the system 100 to identify error(s) that caused the instance to fail.

In some embodiments, the method 1400 includes updating one or more of the pre-programmed elements of the exemplary routine after the initiating implementation step and creating a subsequent instance of the exemplary routine in response to a subsequent request to implement the exemplary routine after the updating step, the subsequent instance of the exemplary routine including an instance of the one or more updated pre-programmed elements of the exemplary routine. For example, in the method 1100 shown in FIG. 11, an administrator 118 updates an exemplary routine corresponding to a currently executing instance of said exemplary routine. The instance of said grouping completes execution based on the grouping prior to the update and subsequent instances of said grouping would execute based on the update from the administrator at step 1114.

In some embodiments, the method 1400 may include simultaneously implementing a plurality of instances of the same exemplary routine. For example, the system 100 is configured to execute, in parallel, a plurality of instances of the same exemplary routine (e.g., four instances of exemplary routine A being executed in parallel). In some embodiments, the method 1400 may include simultaneously implementing at least one instance of the exemplary routine and at least one instance of the subsequent exemplary routine. For example, the system 100 may be configured to execute an instance of an exemplary routine according to method 1100 and simultaneously execute an instance of the updated exemplary routine based on the updates made at step 1114.

In some embodiments, at least some of the instances of the exemplary routine are initiated at a different time than other instances of the same exemplary routine that are being simultaneously implemented. For example, three instances of exemplary routine A may be executed in parallel at a first time, and at a second time different than the first time, a fourth instance of exemplary routine A may be executed. In some embodiments, updating the one or more of the pre-programmed elements includes receiving and storing revised code for performing a task. For example, in step 1114 of method 1100 the updates made to the exemplary routine may include an update to the executable code of a pre-programmed element included in the grouping.

In some embodiments, the method 1400 may include, after the detecting step and before the terminating step, attempting to re-implement at least one instance of the pre-programmed elements associated with the detected error. For example, in steps 816-820 of method 800 an instance of a pre-programmed element, which failed to execute, is retried. In some embodiments an error is detected based upon a pre-defined number attempts to execute an instance of a pre-programmed element. In one embodiment, the pre-defined number of attempts is stored in an attempts field in the database. In some embodiments, each attempt to execute corresponds to an incremented value of a retry count in a retry field (e.g., up to the pre-defined number of retry attempts is performed). In some embodiments, the method 1400 may include detecting a trigger event that triggers, without user intervention, a re-initiation of the performance of the instance of at least one of the pre-programmed elements and wherein an error state that prevents the completion of the at least one instance arises after a subsequent trigger event is detected following a pre-selected number of re-initiations of the performance of the at least one instance of the pre-programmed element.

In some embodiments, the method 1400 may include the steps of defining a retry threshold value for each of the pre-programmed elements, and after the detecting step and before the terminating step, attempting to re-implement the at least one instance of the pre-programmed elements associated with the detected error in accordance with the retry threshold value. For example, in the method 900 shown in FIG. 9, the system 100 is configured to retry an instance of a failed pre-programmed element in steps 916-920 five times.

In some embodiments, the method 1400 may include the steps of during implementation of the instance of the exemplary routine, detecting the absence of prescription authorization data needed to complete the implementation of the instance of the exemplary routine, based on the absence of the prescription authorization, automatically transmitting an authorization form to an authorizing entity, receiving an authorization facsimile of a completed form in response to the automatic transmitting and automatically populating a prescription authorization field based upon the received facsimile. For example, during execution of an instance of an exemplary routine, the system 100 may be configured to determine that there is no record of a prescription authorization required for an instance of a pre-programmed element to perform its intended task. In response, the system 100 may transmit a prescription authorization form to an authorizing entity (e.g., a veterinarian) who then receives and inputs the information required by the prescription authorization form. The authorizing entity may transmit the completed prescription authorization form in the form of a facsimile. The system 100 may be configured to receive the facsimile and automatically update/populate records in database 110 based on the information in the received facsimile.

In some embodiments, the method 1400 includes receiving a datafile containing optical character recognition data associated with the authorization facsimile. For example, the system 100 may be configured to perform optical character recognition on the received facsimile in order to convert the information on the received facsimile to computer readable text which can then be updated/populated in database 110. In some embodiments, the method 1400 may include automatically storing the datafile containing optical character recognition data in a secure database based upon the automatically populating the prescription authorization field. In some embodiments, regular expression matching logic is applied to the datafile containing optical character recognition data to identify data associated with at least one of: owner name, pet name, record identifier for a prescription, clinic name, authorization status, refill authorization data, reason for requiring compound prescription and combinations thereof. In some embodiments, the simultaneously implemented plurality of instances of the exemplary routines are complex operations related to prescription authorization implementations as described herein (e.g., by automatically processing fax prescriptions). In some embodiments, at least 100 complex routines are performed simultaneously per minute.

In some embodiments, the method 1400 further includes the steps of adding or removing at least one selected pre-programmed element from the exemplary routine after the initiating implementation step, and creating a subsequent instance of the exemplary routine in response to a subsequent request to implement the exemplary routine after the adding or removing step, the subsequent instance of the exemplary routine reflecting the addition or removal of the at least one selected pre-programmed element in accordance with the adding or removing step. For example, in step 1114 of method 1100, the administrator 118 may update the exemplary routine having a corresponding instance which is currently executing to remove a pre-programmed element. The instance, which is currently executing, executes based on the grouping and/or exemplary routine prior to the update at step 1114. However, subsequent instances may execute based on the update and would therefore not include an instance of the pre-programmed element which was removed in step 1114 (e.g., the method 700 of FIG. 7 terminating after step 714).

In some embodiments, one or more data objects are not populated at the time of creating of an instance of the exemplary routine but are populated later in order for the instance of the exemplary routine to complete. For example, when selecting a new pre-programmed element an administrator would preferably identify the data that are required for the particular prep-programmed element (e.g., incident data, contact data, organization data shown in FIG. 2). Alternatively, the particular data required by the pre-programmed element may be automatically identified through the execution of separate pre-programmed elements. In one embodiment, when an instance of a pre-programmed element is created at runtime, the system verifies that a record associated with the required data is associated with the request (e.g., the creation of the instance). For example, the system 100 may be configured to use specific data such that the system 100 may verify that a record associated with the specific data is associated with the creation of the instance of the exemplary routine. When an instance of a pre-programmed element requiring the said specific data is requested, the system 100 may be configured to verify that a record associated with the required data elements, stored in database 110, is associated with the request for the instance of the pre-programmed element. In some embodiments, logging exists out-of-band. For example, the system 100 may be configured to, in the event that an instance of a pre-programmed element fails to execute, detect the failure to execute, log the failure to execute, and transmit an indication that the instance of the pre-programmed element failed to execute (e.g., steps 916-924 of method 900).

In some embodiments, the method 1400 includes the steps of receiving from a user, trigger instructions defining at least one trigger condition, and wherein the creating of an instance of the exemplary routine is based upon a recognition that at least one of the trigger conditions has been met. For example, an administrator 118 may, via the admin UI, define incidents that trigger the creation of an instance of an exemplary routine. In some embodiments, at least one trigger condition is a change in data state (e.g., change in underlying data). In some embodiments, each pre-programmed element operates on one or more of: i) a defined data set; and ii) a variable data set (e.g., data populated in a particular data field may change over time). A defined data set may be a row within a database table, stored in database 110, and the associated fields that a pre-programmed element requires for execution. If one or more of the associated fields is null, or has a value that is not expected by the pre-programmed element, the system 100 may be configured to prevent a crash by retrying execution of the instance of the pre-programmed element as described in method 900.

In some embodiments, the method 1400 includes the step of, upon detecting the error that prevents the completion of at least one instance of the pre-programmed elements, receiving an intervention to complete the at least one instance of the pre-programmed element. For example, in steps 926-930 of method 900 a user (e.g., admin 118 or developer 120) resolves the error (e.g., step 926) and resets (e.g., decrements in step 928) the retry count and performs execution of the exemplary routine. In some embodiments, resetting of the retry count is automatically undertaken upon the execution of an intervention. For example, upon resolving the error the system 100 may be configured to automatically reset the retry count. In some embodiments, the exemplary routine may include data object mapping that defines for each exemplary routine the location of data required by one or more pre-programmed elements within the exemplary routine. For example, each exemplary routine may include the ID, and or name of the pre-programmed elements required for the exemplary routine. In some embodiments, the data object mapping is based upon at least one of: i) mapping data received in response to a prompt presented to the user through a user interface; ii) a user selection based upon a predefined menu of mapping options; and iii) indicia associated with a trigger condition induces the creating of an instance of the exemplary routine. For example, an email address required by an instance of a pre-programmed element may be changed. In response to that change, a new instance of the exemplary routine is created (e.g., steps 1214 to 1230 of method 1200). In some embodiments, the data object mapping is at least in part defined within the pre-programmed elements.

In some embodiments, the method 1400 includes the step of simultaneously implementing one or more instances of an exemplary routine by implementing instances of pre-programmed elements in parallel. For example, in step 714 of method 700 different instances of pre-programmed elements are being executed in parallel. Those instances of pre-programed elements may be instances of the same preprogrammed elements included in instances of the same exemplary routine which is being executed by system 100 in parallel.

In some embodiments, the method 1400 includes the step of simultaneously implementing one or more instances of an exemplary routine by implementing instances of pre-programmed elements in series.

In some embodiments, the method 1400 includes the step of sequencing the performance of pre-programmed elements by delaying instructions to implement a pre-programmed element until at least one of another pre-programmed element achieves a predefined state. For example, the instances of pre-programmed elements executed in step 824 do not happen until the instance of the pre-programmed elements in step 820 execute. In some embodiments, the predefined state includes at least one of: i) a completion state; ii) a failure state. In some embodiments, the completion state includes at least a partial completion and the failure state includes failure after a predetermined number of tries. In some embodiments, the completion state includes at least one of: i) complete; ii) partial complete; iii) failed to complete; iv) not started and v) delayed. The failed to complete state may refer to an instance of a pre-programmed element that has failed, prior to a predetermined number of tries occurring, to successfully execute. Put another way, in FIG. 9 steps 916-920, an instance of a pre-programmed element may be retried/attempted up to five times and failed attempts to execute, up to the five times, may result in a "failed to complete" status.

In some embodiments, at least one pre-programmed element is a long-running pre-programmed element that is programmed to cause other pre-programmed elements within an instance of the exemplary routine, in which an instance of the long-running element is included, to at least one of: i) pause execution until the long-running element reaches a completion state; and ii) delay completion until the long-running element reaches the completion state. For example, in steps 1016 to 1020 in method 1000 the method 1000 does not progress past step 1020 until the instance of the pre-programmed element marked as having a locked status in step 1016 is complete.

In some embodiments, the method 1400 includes the steps of: completing the instance of the exemplary routine using the state of the respective instances of pre-programmed elements after the instance of the exemplary routine has been created, wherein subsequent to the time the instance of the exemplary routine has been created, a change is made to the exemplary routine upon which the instance of the exemplary routine is based, and interrupting the instance of the exemplary routine after receiving a call to interrupt the instance of the exemplary routine based upon call to create a new instance of the exemplary routine using a data site that also used by the instance of the exemplary routine and the dataset includes a flag set to cause the interruption of the instance of the exemplary routine.

In some embodiments, the method 1400 includes interrupting execution of the instance of the exemplary routine upon receipt of a triggering event. For example, the method 1200 at step 1216 cancels a pending instance of a pre-programmed element and restarts execution of the instance of the corresponding exemplary routine in response to a change in underlying records at step 1214. In some embodiments, the method 1400 includes interrupting execution of the instance of the exemplary routine upon receipt of a predetermined number of triggering events including at least one of: i) a network timeout; ii) a system error. In some embodiments, the triggering event includes one or more of: i) a change to a data record; or ii) a change to the pre-programmed element. In some embodiments, each pre-programmed element is fully executable without being directly dependent upon data generated by of any other pre-programmed element. In some embodiments, the instance of the exemplary routine reaches a successful conclusion if all of the pre-programmed elements within the instance of the exemplary routine are completed.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. A method for performing a fault tolerant automated sequence of computer implemented tasks comprising:
   at a processing server coupled to a database and a storefront server:
   render an administrator facing UI at a client device coupled to the processing server;
   presenting for selection by a user via the administrator facing UI a plurality of pre-programmed elements, each pre-programmed element being independently executable relative each other pre-programmed element such that an output of any of the pre-programmed elements is not a direct input to any other of the pre-programmed elements;
   receiving via the administrator facing UI a selection of two or more of the pre-programmed elements and a sequence for performing each pre-programmed elements in the selection to form an exemplary routine;
   receiving from the storefront server an indication of a trigger event corresponding to an input at the customer facing UI, and in response to receiving the indication of a trigger event, automatically creating an instance of the exemplary routine, the instance of the exemplary routine including an instance of each of the selected pre-programmed elements arranged for performance in accordance with the sequence and being configured to perform tasks defined by the pre-programmed elements and the sequence, the instance of the exemplary routine further including a status indicator indicating an execution status of each instance of each of the selected pre-programmed elements, the execution status of each instance of each of the selected pre-programmed elements being initially set to a pending execution status;

at a monitoring server coupled to the processing server and the database, and at a pre-defined interval:
querying the database to identify instances of pre-programmed elements having a pending execution status;
in response to the querying the database, receiving from the database the identity of instances of pre-programmed elements having a pending execution status;
transmitting a request to the processing server to initiate execution of the identified instances of pre-programmed elements according to the sequence; and at the processing server, automatically executing the identified instances of the pre-programmed elements according to the sequence in response to the request from the monitoring server.

2. The method of claim 1 further comprising:
detecting an error that prevents completion of at least one instance of the pre-programmed elements; and
terminating the execution of the instance of the exemplary routine upon detection of the error without user intervention.

3. The method of claim 2 further comprising:
after the detecting step and before the terminating step, attempting to re-execute at least one instance of the pre-programmed elements associated with the detected error.

4. The method of claim 2 further comprising:
detecting a trigger event that triggers, without user intervention, a re-execution of the instance of at least one of the pre-programmed elements and wherein an error state that prevents the completion of the at least one instance arises after a subsequent trigger event is detected following a pre-selected number of re-executions of the at least one instance of the pre-programmed element.

5. The method of claim 2 further comprising:
defining a retry threshold value for each of the pre-programmed elements; and
after the detecting step and before the terminating step, attempting to re-execute the at least one instance of the pre-programmed elements associated with the detected error in accordance with the retry threshold value.

6. The method of claim 1 further comprising:
during execution of the instance of the pre-programmed element, detecting the absence of prescription authorization data needed to complete the execution;
based on the absence of the prescription authorization, automatically transmitting an authorization form to an authorizing entity;
receiving an authorization facsimile of a completed form in response to the automatic transmitting; and
automatically populating a prescription authorization field based upon the received facsimile.

7. The method of claim 6 further comprising:
receiving a datafile containing optical character recognition data associated with the authorization facsimile.

8. The method of claim 7 further comprising:
automatically storing the datafile containing optical character recognition data in a secure database based upon the automatically populating the prescription authorization field.

9. The method of claim 7, wherein regular expression matching logic is applied to the datafile containing optical character recognition data to identify data associated with at least one of: owner name, pet name, record identifier for a prescription, clinic name, authorization status, refill authorization data, reason for requiring compound prescription and combinations thereof.

10. The method of claim 1 further comprising:
simultaneously executing one or more instances of instances of pre-programmed elements in parallel.

11. The method claim 1, wherein at least one pre-programmed element is a long-running pre-programmed element that is programmed to cause other pre-programmed elements within an instance of the exemplary routine in which an instance of the long-running element is included to at least one of: i) pause execution until the long-running element reaches a completion state; ii) delay completion until the long-running element reaches the completion state.

12. The method of claim 1, wherein each pre-programmed element is fully executable without being directly dependent upon the execution of any other pre-programmed element.

13. The method of claim 1, wherein a failure to execute one instance of one of the pre-programmed elements does not prevent the execution and completion of another instance of the same pre-programmed element.

14. A system for implementing a fault tolerant automated sequence of computer implemented tasks comprising:
a storefront server configured to cause a customer facing user interface (UI) display to render at one or more customer devices and to receive one or more inputs via the customer facing UI
a database, coupled to the storefront server and configured to store pre-programmed elements that each include an independently executable self-contained unit of computer code configured to perform a specific task; and
a processing server coupled to the database and the storefront server, the processing server having a central processing unit, memory, an input port, and an output port, the processing server being further coupled to a plurality of client devices, the processing server being configured to:
cause the client device to render an administrator facing UI at a client device of the plurality of client devices;
present for selection by a user via the administrator facing UI a plurality of the pre-programmed elements, each pre-programmed element being independently executable relative each other pre-programmed element such that an output of any of the pre-programmed elements is not a direct input to any other of the pre-programmed elements;
receive via the administrator facing UI a selection of Two or more of the pre-programmed elements and a sequence for performing each pre-programmed element in the selection to form an exemplary routine;
receive from the storefront server an indication of a trigger event corresponding to an input at the customer facing UI, and in response to receiving the indication of a trigger event, automatically create an instance of the exemplary routine, the instance of the exemplary routine including an instance of each of the selected pre-programmed elements arranged for performance in accordance with the sequence and being configured to perform tasks defined by the pre-programmed elements and the sequence, the instance of the exemplary routine further including a status indicator indicating an execution status of each instance of each of the selected pre-programmed elements, the execution status of each instance of each of the selected pre-programmed elements being initially set to a pending execution status; and a monitoring server coupled to the processing server and database, the monitoring server configured to, at a pre-defined interval:

query the database to identify instances of pre-programmed elements having a pending execution status;

in response to the query, receive from the database the identity of instances of pre-programmed elements having a pending execution status; and transmit a request to the processing server to initiate execution of the identified instances of pre-programmed elements according to the sequence, wherein the processing server is further configured to automatically execute the identified instances of the pre-programmed elements according to the sequence in response to the request from the monitoring server.

15. The system of claim 14, wherein the processing server is further configured to:

detect an error that prevents completion of at least one instance of the pre-programmed elements; and terminate the execution of the associated instance of the exemplary routine upon detection of the error without user intervention.

16. The system of claim 15, wherein the processing server is further configured to:

after detecting the error and prior to terminating implementation of the instance, attempt to re-implement at least one instance of the pre-programmed elements associated with the detected error.

17. The system of claim 15, wherein the processing server is further configured to:

detecting a trigger event that triggers, without user intervention, a re-initiation of the instance of at least one of the pre-programmed elements and wherein an error state that prevents the completion of the at least one instance arises after a subsequent trigger event is detected following a pre-selected number of re-initiations of the performance of the at least one instance of the pre-programmed element.

18. The system of claim 15, wherein the processing server is further configured to:

define a retry threshold value for each of the pre-programmed elements; and after detecting the error and prior to terminating execution of the instance, attempt to re-execute the at least one instance of the pre-programmed elements associated with the detected error in accordance with the retry threshold value.

19. The system of claim 14, wherein the processing server is further configured to:

during execution of the instance of the exemplary routine, detect the absence of prescription authorization data needed to complete the execution of the instance of the exemplary routine;

based on the absence of the prescription authorization, automatically transmit an authorization form to an authorizing entity;

receive an authorization facsimile of a completed form in response to the automatic transmitting; and automatically populate a prescription authorization field in the database based upon the received facsimile.

20. The system of claim 19, wherein the processing server is further configured to:

receive a datafile containing optical character recognition data associated with the authorization facsimile.

21. The system of claim 20, wherein the processing server is further configured to:

automatically store the datafile containing optical character recognition data in a secure database based upon the automatically populating the prescription authorization field.

22. The system of claim 20, wherein regular expression matching logic is applied to the datafile containing optical character recognition data to identify data associated with at least one of: owner name, pet name, record identifier for a prescription, clinic name, authorization status, refill authorization data, reason for requiring compound prescription and combinations thereof.

23. The system of claim 14, wherein the processing server is further configured to:

simultaneously execute one or more instances of pre-programmed elements in parallel.

24. The system of claim 14, wherein at least one pre-programmed element is a long-running pre-programmed element that is programmed to cause other pre-programmed elements within an instance of the associated exemplary routine in which an instance of the long-running element is included to at least one of: i) pause execution until the long-running element reaches a completion state; ii) delay completion until the long-running element reaches the completion state.

25. The system of claim 14, wherein each pre-programmed element is fully executable without being directly dependent upon the execution of any other pre-programmed element.

26. The system of claim 14, wherein a failure of an execution of one instance of one of the pre-programmed elements does not prevent the execution and completion of another instance of the same pre-programmed element.

* * * * *